US007560444B2

(12) United States Patent
Richardson et al.

(10) Patent No.: US 7,560,444 B2
(45) Date of Patent: Jul. 14, 2009

(54) POLYSACCHARIDES FOR PULMONARY DELIVERY OF ACTIVE AGENTS

(75) Inventors: Thomas Richardson, South Boston, MA (US); Ganesh Venkataraman, Bedford, MA (US); Yiwei Qi, Andover, MA (US); Michele Picard, Dover, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 225 days.

(21) Appl. No.: 10/957,218

(22) Filed: Oct. 1, 2004

(65) Prior Publication Data

US 2005/0207988 A1 Sep. 22, 2005

Related U.S. Application Data

(60) Provisional application No. 60/580,869, filed on Jun. 18, 2004, provisional application No. 60/508,062, filed on Oct. 1, 2003.

(51) Int. Cl.

*A61K 31/727* (2006.01)
*C08B 37/10* (2006.01)
*C12P 19/04* (2006.01)
*C07H 5/00* (2006.01)

(52) U.S. Cl. ....................... 514/56; 536/123; 536/123.1

(58) Field of Classification Search .................... 514/56
See application file for complete search history.

(56) References Cited

U.S. PATENT DOCUMENTS 5,250,519 A 10/1993 Conrad et al.
5,280,016 A 1/1994 Conrad et al.
5,474,987 A * 12/1995 Cohen et al. .................. 514/56
5,952,008 A 9/1999 Backstrom et al.
5,972,331 A 10/1999 Reichert et al.
5,993,783 A 11/1999 Eljamal et al.
6,019,968 A 2/2000 Platz et al.
6,051,256 A 4/2000 Platz et al.
6,123,936 A 9/2000 Platz et al.
6,165,463 A 12/2000 Platz et al.
6,231,851 B1 5/2001 Platz et al.
2002/0141946 A1* 10/2002 Schmitke et al. .............. 424/46
2003/0068279 A1 4/2003 Platz et al.
2003/0086877 A1 5/2003 Platz et al.
2003/0198601 A1 10/2003 Platz et al.
2004/0009231 A1* 1/2004 Jackson et al. .............. 424/489

FOREIGN PATENT DOCUMENTS

WO WO 02/32406 A2 4/2002
WO WO 03/068187 8/2003
WO WO 03/068188 8/2003

OTHER PUBLICATIONS

Huhle et al. "Comparison of Three Heparin Bovine Serum Albumin Binding Methods for Production of Antiheparin Antibodies" Seminars in Thrombosis and Hemostasis (1994) vol. 20, No. 2, pp. 193-204.*
Thorpe et al., "Heparin-Steroid Conjugates: New Angiogenesis Inhibitors with Antitumor Activity in Mice" Cancer Research (1993) vol. 53, pp. 3000-3007.*
Bath, "Low Molecular Weight Heparin in Acute Stroke" Expert Opinion on Investigational Drugs, (1998) pp. 1323-1330.*
Merck Manual of Diagnosis and Therapy, seventeenth Edition, published 1999 by Merck Research Laboratories, Beers and Berkow, Eds. pp. pp. 1865-1868.*
2006 Chemical Abstracts Catalog, Published py Chemical Abstracts Service, p. 52.*
Bath, P.M.W., "Low Molecular Weight Heparin in Acute Stroke" Exp. Opin. on Invest. Drugs 1998 vol. 7, No. 8, pp. 1323-1330.
Thorpe, P.E. et al., "Heparin-Steroid Conjugates: New Angiogenesis Inhibitors with Antitumor Activity in Mice" Cancer Research Jul. 1993 vol. 53, pp. 3000-3007.
Huhle, G. "Comparison of Three Heparin Bovine Serum Albumin Binding Methods for Production of Antiheparin Antibodies" Seminars in Thrombosis and Hemostasis, vol. 20, No. 2 1994 pp. 193-204.
International Search Report and Written Opinion dated Apr. 9, 2007.
Supplementary European Search Report dated Sep. 10, 2008.

* cited by examiner

*Primary Examiner*—Shaojia Anna Jiang
*Assistant Examiner*—Eric S Olson
(74) *Attorney, Agent, or Firm*—Lando & Anastasi, LLP

(57) ABSTRACT

Formulation for pulmonary delivery of a therapeutic, prophylactic, or diagnostic agent including a low molecular weight heparin and a therapeutic, prophylactic, or diagnostic agent.

43 Claims, 8 Drawing Sheets

POLYSACCHARIDES FOR PULMONARY DELIVERY OF ACTIVE AGENTS

CLAIM OF PRIORITY

This application claims priority under 35 USC §119(e) to U.S. patent application Ser. No. 60/580,869, filed on Jun. 18, 2004, and U.S. patent application Ser. No. 60/508,062, filed on Oct. 1, 2003, the entire contents of each of which are hereby incorporated by reference.

SUMMARY OF THE INVENTION

The present invention is based, in part, on the discovery that polysaccharides, particularly HLGAG's, such as heparin and low molecular weight heparin (LMWH) deliver active agents, regardless of the size of the active agent, through pulmonary tissue at therapeutically and prophylactically effective levels. It has been found that saccharide structures associated with polysaccharides that play a role in upper lung activity, e.g., normal physiology and homeostasis of the upper lung, can be used to enhance delivery of active agents through the pulmonary tissue.

Accordingly, in one aspect, the invention features a preparation, e.g., a purified preparation, of a polysaccharide, e.g., an HLGAG, such as heparin, e.g., LMWH, which has been modified as is described herein. In another embodiment, the polysaccharide is a polysaccharide or a portion thereof involved in an activity of the lung, e.g., normal physiology and/or homeostasis of the lung (e.g., one or more of hydration, epithelial integrity and tight junction barrier functions).

In a preferred embodiment the polysaccharide is a LMWH and is chosen from the group of: enoxaparin, dalteparin, reviparin, tinzaparin, nadroparin, certoparin, ardeparin, and parnaparin.

In one embodiment, the polysaccharide consists of about two, three, four, five, six, seven, eight, nine, ten, eleven, twelve, thirteen, fourteen, fifteen, sixteen, seventeen, eighteen, nineteen or twenty disaccharides. It is particularly preferred that the polysaccharide is a hexasaccharide or larger, and even more preferrably, an octasaccharide or larger.

In one embodiment, the polysaccharide is modified such that the size of the polysaccharide is reduced as compared to a reference standard, e.g., a commercially available version of the polysaccharide or a polysaccharide from which the modified polysaccharide is derived, e.g., the polysacaride prior to modification. The size of the polysaccharide can be reduced, e.g., by at least 5%, 10%, 15%, 20%, 30%, 40%, 50%, 60%, 70% or more as compared to the reference standard. In one embodiment, the size of the provided polysaccharide can be reduced, e.g., by digesting the polypeptide with at least one agent, e.g., an agent selected based upon the chemical signature of the polysaccharide. For example, the agent can be an enzyme (e.g., an enzyme which is capable of cleaving the polysaccharide at known locations in the polysaccharide based upon its chemical signature) or a chemical (e.g., a chemical capable of cleaving the polysaccharide at known locations in the polysaccharide based upon its chemical signature) or, a chemical providing selective functional group modification, or combinations thereof. Examples of enzymes which can be used include heparin degradation enzymes, e.g., heparin lysase such as heparinase I, heparinase II, heparinase III, heparinase IV, heparanase, and functionally active fragments and variants thereof. Examples of chemicals that can be used include oxidative depolymerization with $H_2O_2$ or $Cu^+$ and $H_2O_2$, deaminative cleavage with isoamyl nitrite, or nitrous acid, β-eliminative cleavage with benzyl ester of heparin by alkaline treatment or by heparinase. Examples of chemicals for selective functional group changes include: 2-O desulfonation by treatment with base, such as NaOH, and lyophilization; N-desulfonation with pyridine and DMSO; N+O desulfonation with pyridine and DMSO/dioxane/methanol; 6-O desulfonation with pyridine and NMP/$H_2O$; 3-O sulfonation with $SO_3$/trimethylamine/$H_2O$; and other approaches known in the art.

In another embodiment, the polysaccharide is modified such that the charge of the polysaccharide is modified, e.g., increased or decreased, as compared to a reference standard, e.g., a commercially available version of the polysaccharide or a polysaccharide from which the modified polysaccharide is derived. Decreasing the charge of a polysaccharide is also referred to herein as "neutralizing" the charge. In some embodiments, when the charge of the polysaccharide is neutralized, the net negative or net positive charge of the polysaccharide can be reduced by at least 10%, 20%, 30%, 40%, 50%, 60%, 70%, 80%, or 90%. In other embodiments, when the charge of the polysaccharide is neutralized, it can be neutralized such that there is a net negative and net positive charge of 0. The polysaccharide can be neutralized, e.g., by digesting the polypeptide with at least one agent, e.g., an agent selected based upon the chemical signature of the polysaccharide. For example, the agent can be an enzyme (e.g., an enzyme which is capable of cleaving the polysaccharide at known locations in the polysaccharide based upon its chemical signature) or a chemical (e.g., a chemical capable of cleaving the polysaccharide at known locations in the polysaccharide based upon its chemical signature and/or a chemical capable of providing a selective functional group modification) or combinations thereof. Examples of enzymes which can be used include heparin degradation enzymes, e.g., heparin lysase such as heparinase I, heparinase II, heparinase III, heparinase IV, heparanase, and functionally active fragments and variants thereof. Examples of chemicals that can be used include oxidative depolymerization with $H_2O_2$ or $Cu^+$ and $H_2O_2$, deaminative cleavage with isoamyl nitrite, or nitrous acid, β-eliminative cleavage with benzyl ester of heparin by alkaline treatment or by heparinase. Other examples include chemicals for selective functional group changes: 2-O desulfonation by treatment with base, such as NaOH, and lyophilization; N-desulfonation with pyridine and DMSO; N+O desulfonation with pyridine and DMSO/dioxane/methanol; 6-O desulfonation with pyridine and NMP/$H_2O$; 3-O sulfonation with $SO_3$/trimethylamine/$H_2O$; and other approaches known in the art.

In other embodiments, when the charge of the polysaccharide is neutralized, it can be neutralized by contacting the polysaccharide with a charge neutralizing agent, e.g., a counter ion such as mono- or divalent ion, (e.g., barium, calcium, sodium, potassium, lithium, ammonium, magnesium, zinc), a transition metal (e.g., iron, nickel and copper), and/or other neutralizing compounds (e.g., a small organic compound, spermine, spermidine, low molecular weight protamine, basic peptides).

In other embodiments, the net charge of the polysaccharide is increased, e.g., by increasing the charge density. The charge density can be increased, e.g., by removing one or more low charged domains, e.g., by the addition of one or more sulfate group, and/or other charged species, such as phosphates, acetates, etc. In some embodiments, sulfate groups and/or other charged species can be added by one or more of: enzymatic, chemical, or physical means.

In some embodiments, a chemical signature of the polysaccharide from which the polysaccharide is derived has been determined and the polysaccharide is modified based upon its chemical signature. The chemical signature of the polysaccharide can be used, e.g., to modify the polysaccharide to reduce one or more therapeutic activities of the polysaccharide, to modify the size and/or to modify the charge of the polysaccharide. In other embodiments, a chemical signature of the polysaccharide can been determined. Information regarding the chemical signature of a polysaccharide can be used, e.g., to determine whether another polysaccharide is likely to have similar delivery properties as the polysaccharide or to determine whether another polysaccharide is not likely to have similar delivery properties as the polysaccharide. In some embodiments, the chemical signature of the polysaccharide is compared to a chemical signature of a polysaccharide involved in lung activity, e.g., normal physiology and/or homeostasis of the lung. The invention can include modifying the polysaccharide based upon similarities and/or differences between the chemical signature of the polysaccharide and the polysaccharide or polysaccharides involved in lung activity.

In a preferred embodiment the polysaccharide is modified such that at least one therapeutic activity of the polysaccharide is reduced by at least 40%, 50%, 60%, 70%, 80%, 90%, 95%, 99% or more as compared to a reference standard. In some embodiments, the reference standard is the level of therapeutic activity of a commercially available version of the polysaccharide or is the level of therapeutic activity of the polysaccharide prior modification.

In some embodiments, the polysaccharide is linked to an active agent, e.g., a therapeutic, diagnostic, or prophylactic agent. Active agents can include a therapeutic or prophylactic polypeptide, nucleic acid, small molecule, lipid/glycolipids, etc. In one embodiment, the active agent is a therapeutic polypeptide selected from the group consisting of insulin, proinsulin, human growth hormone, interferon, α-1 proteinase inhibitor, alkaline phosphotase, angiogenin, cystic fibrosis transmembrane conductance regulator, extracellular superoxide dismutase, fibrinogen, glucocerebrosidase, glutamate decarboxylase, human serum albumin, myelin basic protein, soluble CD4, lactoferrin, lactoglobulin, lysozyme, lactoalbumin, erythropoietin, tissue plasminogen activator, antithrombin III, prolactin, and α1-antitrypsin. The therapeutic or prophylactic polypeptide can be an active derivative or fragment of such polypeptides. The active agent can also be, but is not limited to one or more of: parathyroid hormone and derivatives and fragments thereof, erythropoietin, epoetin beta, gene activated erythropoietin, second generation EPO, novel erythropoiesis stimulating protein, insulin lispro, insulin (bovine), insulin, insulin aspart, insulin analogue, Calcitonin, Theraccine, becaplermin (recombinant human platelet derived growth factor-BB), trafermin, human growth hormone-releasing factor, BMP-7, PEG aspariginase, domase alpha, alglucerase, agalsidase-beta, domase alpha, agalsidase-alfa, streptokinase, teneteplase, reteplase, alteplase, pamiteplase, Rh factor VIII, Rh FVIIa, Factor IX (Human), Factor IX (complex), HGH, Somatrem/somatropin, anti-CD33-calicheamicin conjugate, Edrecolomab, rituxumab, daclizumab, trastuzumab, sulesomab, abciximab, infliximab, muromonab-CD3, palivizumab, alemtuzumab, basiliximab, oprelvekin, gemtuzumab ozogamicin, ibritumomab tiuxetan, sulesomab, palivizumab, interleukin-2, celmoleukin (rIL-2), interferon alfacon-1, interferon alpha, interferon alpha+ribavirin, peg interferon alpha-2a, interferon alpha-2b, interferon alpha 3n, interferon beta-1a, interferon beta, interferon beta 1b, interferon gamma, interferon gamma-1b, filgrastim, sargramostim, lenograstim, molgramostim, mirimostim, nartograstim, oprelvekin, peptide tyrosin-tyrosin (PYY), apolipoprotein A-IV, leptin, melanocortin, amylin, orexin, adiponectin, and ghrelin. In one embodiment, the active agent is an active polypeptide, e.g., a therapeutic or prophylactic polypeptide, and the polypeptide has a molecular weight of less than 150 kDa, more preferrably less than 100 kDa, and more preferrably less than 50 kDa. In one embodiment, the active agent is an active polypeptide, e.g., a therapeutic or prophylactic polypeptide, and the polypeptide has a molecular weight of about 500 Da-5 kDa, 5 to 10 kDa, 10 to 30 kDa, 18 to 35 kDa, 30 to 50 kDa, 50 to 100 kDa, 100 to 150 kDa. In one embodiment, the active polypeptide is insulin or an active fragments or derivatives thereof. In another embodiment, the active polypeptide is human growth hormone or an active fragment or derivative thereof. In yet another embodiment, the active polypeptide is interferon.

In other embodiments, the polysaccharide is linked to an inactive agent. Examples of inactive agents include biological probes or contrast agents for imaging.

In another embodiment, the active agent can be a small molecule drug, e.g., a small molecule drug currently available for therapeutic, diagnostic, or prophylactic use, or a drug in development. In some embodiments, the active agent is linked to one or more polysaccharides in the formulation. As an example, small molecule drugs, and protein-based drugs may be linked to polysaccharides for delivery via known chemistries such as EDC, $CNBH_4$/DMSO/Acetic Acid, etc.

In another aspect, the invention features a formulation, preferably for pulmonary delivery, of a therapeutic, diagnostic, or prophylactic agent. The formulation include a polysaccharide, e.g., a polysaccharide described herein, and an active agent, e.g., a therapeutic, diagnostic or prophylactic agent. Preferred polysaccharides are, e.g., an HLGAG, such as heparin or low molecular weight heparin. In a preferred embodiment the polysaccharide is a LMWH and is chosen from the group of: enoxaparin, dalteparin, reviparin, tinzaparin, nadroparin, certoparin, ardeparin, and pamaparin.

Therapeutic and prophylactic agents include therapeutic or prophylactic polypeptides, nucleic acids, small molecule, lipid/glycolipids, etc. In one embodiment, the active agent is a therapeutic polypeptide selected from the group consisting of insulin, proinsulin, human growth hormone, interferon, α-1 proteinase inhibitor, alkaline phosphotase, angiogenin, cystic fibrosis transmembrane conductance regulator, extracellular superoxide dismutase, fibrinogen, glucocerebrosidase, glutamate decarboxylase, human serum albumin, myelin basic protein, soluble CD4, lactoferrin, lactoglobulin, lysozyme, lactoalbumin, erythropoietin, tissue plasminogen activator, antithrombin III, prolactin, and α1-antitrypsin. In another embodiment, the active agent can include, but is not limited to, one or more of: parathyroid hormone and derivatives and fragments thereof, erythropoietin, epoetin beta, gene activated erythropoietin, epoetin beta, second generation EPO, epoetin beta, novel erythropoiesis stimulating protein, insulin lispro, insulin (bovine), insulin, insulin aspart, insulin analogue, Calcitonin, Theraccine, becaplermin (recombinant human platelet derived growth factor-BB), trafermin, human growth hormone-releasing factor, BMP-7, PEG aspariginase, domase alpha, alglucerase, agalsidase-beta, dornase alpha, agalsidase-alfa, streptokinase, teneteplase, reteplase, alteplase, pamiteplase, Rh factor VIII, Rh FVIIa, Factor IX (Human), Factor IX (complex), HGH, Somatrem/somatropin, anti-CD33-calicheamicin conjugate, Edrecolomab, rituxumab, trastuzumab, daclizumab, sulesomab, abciximab, infliximab, muromonab-CD3, palivizumab, alemtuzumab, basiliximab, oprelvekin, gemtuzumab ozogamicin, ibritumomab tiuxetan, sulesomab, palivizumab, interleukin-2, celmoleukin (rIL-2), interferon alfacon-1, interferon alpha, interferon alpha+ribavirin, PEG interferon alpha-2a, interferon alpha-2b, interferon alpha 3n, interferon beta-1a, interferon beta, interferon beta 1b, interferon gamma, interferon gamma-1b, filgrastim, lenograstim, sargramostim, molgramostim, mirimostim, nartograstim, oprelvekin, peptide tyrosin-tyrosin (PYY), apolipoprotein A-IV, leptin, melanocortin, amylin, orexin, adiponectin, and ghrelin. Other polypeptides, collectively "adipokines", are those implicated in regulating satiety, including peptide tyrosine-tyrosine (PYY), apolipoprotein A-IV, leptin, melanocortin, amylin, orexin, adiponectin and ghrelin. The therapeutic or prophylactic polypeptide can be an active derivative or fragment of such polypeptides. In one embodiment, the active agent is an active polypeptide, e.g., a therapeutic or prophylactic polypeptide, and the polypeptide has a molecular weight of less than 150 kDa, more preferably less than 100 kDa, and more preferably less than 50 kDa. In one embodiment, the active agent is an active polypeptide, e.g., a therapeutic or prophylactic polypeptide, and the polypeptide has a molecular weight of about 500 Da-5 kDa, 5 to 10 kDa, 10 to 30 kDa, 18-35 kDa, 30 to 50 kDa, 50 to 100 kDa, 100 to 150 kDa. In one embodiment, the active polypeptide is insulin or an active fragments or derivatives thereof. In another embodiment, the active polypeptide is human growth hormone or an active fragment or derivative thereof. In yet another embodiment, the active polypeptide is interferon or active fragments or derivatives thereof.

In another embodiment, the active agent can be a small molecule drug, e.g., a small molecule drug currently available for therapeutic, diagnostic, or prophylactic use, or a drug in development. In some embodiments, the active agent is admixed with the polysaccharide. Admixtures can be prepared, e.g., by mixing, covalently-linked polysaccharides, ionically-linked polysaccharides, spraying drying and other techniques known in the art. In other embodiments, the active agent is linked to one or more polysaccharide in the formulation. As an example, small molecule drugs, and protein-based drugs may be linked to polysaccharides for delivery via known chemistries such as EDC, $CNBH_4$/DMSO/Acetic Acid, etc.

In other embodiments, the formulation includes a polysaccharide, e.g., a polysaccharide described herein, and an inactive agent. Examples of inactive agents include biological probes or contrast agents for imaging.

In some embodiments, the formulation is a dry formulation. In some embodiments, the dry formulation includes polysaccharide particles having a mean geometric diameter of 1 to 500 microns, e.g., particles having a mean geometric diameter of at least 2, 3, 4, 5, 10, 15, 20, 25, 30, 35, 40, 45, 50 or 100 microns. In other embodiments, the formulation is a liquid formulation (e.g., an aerosol, mist, or a suspension).

In some embodiments, the formulation further includes one or more delivery enhancers, e.g., one or more of a surfactant, an absorption enhancer, protease inhibitor, etc.

In some embodiments, the formulation is provided in a device for pulmonary delivery, e.g., a pressurized or non-pressurized container or dispenser, e.g., a pressurized contained or dispenser which contains a suitable propellant and/or nebulizer, or is user activated. In one embodiment, the formulation is provided in a delivery device for pulmonary delivery that delivers a metered dose of the formulation to a subject.

In another aspect, the invention features a formulation for pulmonary delivery of a therapeutic or prophylactic agent that includes a heterogeneous population of polysaccharides. Preferred polysaccharides comprise HLGAG's, such as heparin or low molecular weight heparin. In a preferred embodiment the polysaccharide is a LMWH and is chosen from the group of: enoxaparin, dalteparin, reviparin, tinzaparin, nadroparin, certoparin, ardeparin, and pamaparin.

In one embodiment, all or a portion of the polysaccharides of the population consist of about two, three, four, five, six, seven, eight, nine, ten, eleven, twelve, thirteen, fourteen, fifteen, sixteen, seventeen, eighteen, nineteen or twenty disaccharides. It is particularly preferred that the polysaccharide is a hexasaccharide or larger, and even more preferrably, an octasaccharide or larger.

In one embodiment, the polysaccharide population is modified such that the size of all or a portion of the polysaccharides is reduced as compared to a reference standard, e.g., a commercially available version of the polysaccharide population or a polysaccharide population from which the modified polysaccharide is derived. The size of all or a portion of the polysaccharides can be reduced, e.g., by at least 5%, 10%, 15%, 20%, 30%, 40%, 50%, 60%, 70% or more as compared to the reference standard. In one embodiment, the size of all or a portion of the provided polysaccharide population can be reduced, e.g., by digesting the polypeptides with at least one agent, e.g., an agent selected based upon the chemical signature of one or more of the polysaccharides of the population. For example, the agent can be an enzyme (e.g., an enzyme which is capable of cleaving polysaccharides at known locations in the polysaccharide based upon its chemical signature) or a chemical (e.g., a chemical capable of cleaving polysaccharides at known locations in the polysaccharide based upon its chemical signature) or combinations thereof. Examples of enzymes which can be used include heparin degradation enzymes, e.g., heparin lysase such as heparinase I, heparinase II, heparinase III, heparinase IV, heparanase, and functionally active fragments and variants thereof. Examples of chemicals which can be used include oxidative depolymerization with $H_2O_2$ or $Cu^+$ and $H_2O_2$, deaminative cleavage with isoamyl nitrite, or nitrous acid, β-eliminative cleavage with benzyl ester of heparin by alkaline treatment or by heparinase. Other examples include chemicals for selective functional group changes: 2-O desulfonation by treatment with base, such as NaOH and lyophilization; N-desulfonation with pyridine and DMSO; N+O desulfonation with pyridine and DMSO/dioxane/methanol; 6-O desulfonation with pyridine and NMP/$H_2O$; 3-O sulfonation with $SO_3$/trimethylamine/$H_2O$; and other approaches known in the art.

In another embodiment, the population of polysaccharide is modified such that the charge of all or a portion of the polysaccharides in the population is modified, e.g., increased or decreased, as compared to a reference standard, e.g., a commercially available version of the polysaccharide population or a polysaccharide population from which the modified polysaccharide is derived. Decreasing the charge of a polysaccharide is also referred to herein as "neutralizing" the charge. In some embodiments, when the charge of the polysaccharide is neutralized, the net negative or net positive charge of the polysaccharide can be reduced by at least 10%, 20%, 30%, 40%, 50%, 60%, 70%, 80%, or 90%. In other embodiments, when the charge of the polysaccharide is neutralized, it can be neutralized such that there is a net negative and net positive charge of 0. The polysaccharide population can be neutralized, e.g., by digesting the polypeptide population with at least one agent, e.g., an agent selected based upon the chemical signature of one or more of the polysaccharides in the population. For example, the agent can be an enzyme (e.g., an enzyme which is capable of cleaving polysaccharides at known locations in the polysaccharide based upon its chemical signature) or a chemical (e.g., a chemical capable of cleaving polysaccharides at known locations in the polysaccharide based upon its chemical signature and/or a chemical providing selective functional group modification) or combinations thereof. Examples of enzymes which can be used include heparin degradation enzymes, e.g., heparin lysase such as heparinase I, heparinase II, heparinase III, heparinase IV, heparanase, and functionally active fragments and variants thereof. Examples of chemicals which can be used include oxidative depolymerization with $H_2O_2$ or $Cu^+$ and $H_2O_2$, deaminative cleavage with isoamyl nitrite, or nitrous acid, β-eliminative cleavage with benzyl ester of heparin by alkaline treatment or by heparinase. Other examples include chemicals for selective functional group changes: 2-O desulfonation by treatment with base, such as NaOH, and lyophilization; N-desulfonation with pyridine and DMSO; N+O desulfonation with pyridine and DMSO/dioxane/methanol; 6-O desulfonation with pyridine and NMP/$H_2O$; 3-O sulfonation with $SO_3$/trimethylamine/$H_2O$; and other approaches known in the art. In other embodiments, when the charge of one or more polysaccharides of the population is neutralized, it can be neutralized by contacting the polysaccharide population with a charge neutralizing agent, e.g., a counter ion such as mono- or divalent ion, (e.g., barium, calcium, sodium, potassium, lithium, ammonium, magnesium, zinc), a transition metal (e.g., iron, nickel and copper), and/or other neutralizing compounds (e.g., a small organic compound, spermine, spermidine, low molecular weight protamine, basic peptides).

In other embodiments, the net charge of the polysaccharide is increased, e.g., by increasing the charge density. The charge density can be increased, e.g., by removing one or more low charged domains, e.g., by the addition of one or more sulfate group, and/or other charged species, such as phosphates, acetates, etc. In some embodiments, sulfate groups and/or other charged species can be added by one or more of: enzymatic, chemical, or physical means.

In some embodiments, a chemical signature of one or more of the polysaccharides of the population from which the polysaccharide is derived has been determined and the polysaccharide is modified based upon its chemical signature. The chemical signature of the polysaccharide can be used, e.g., to modify the polysaccharide to reduce one or more therapeutic activities of the polysaccharide population, to modify the size and/or to modify the charge of one or more polysaccharides in the population. In other embodiments, a chemical signature of one or more of the polysaccharide can been determined. Information regarding the chemical signature of a polysaccharide can be used, e.g., to determine whether another polysaccharide is likely to have similar delivery properties as the polysaccharide or to determine whether another polysaccharide is not likely to have similar delivery properties as the polysaccharide. In some embodiments, the chemical signature of one or more of the polysaccharides of the population is compared to a chemical signature of a polysaccharide involved in lung activity, e.g., normal physiology and/or homeostasis of the lung. The invention can include modifying the polysaccharide based upon similarities and/or differences between the chemical signature of the polysaccharide and the polysaccharide or polysaccharides involved in lung activity.

In a preferred embodiment the population is modified such that at least one therapeutic activity of the population of polysaccharide is reduced by at least 40%, 50%, 60%, 70%, 80%, 90%, 95%, 99% or more as compared to a reference standard. In some embodiments, the reference standard is the level of therapeutic activity of a commercially available version of the polysaccharide population or is the level of therapeutic activity of the polysaccharide population prior modification.

In some embodiments, the formulation further includes an active agent, e.g., an active agent described herein, e.g., therapeutic, diagnostic, or prophylactic agent described herein. The therapeutic or prophylactic polypeptide can be an active derivative or fragment of such polypeptides. In one embodiment, the active agent is an active polypeptide, e.g., a therapeutic or prophylactic polypeptide, and the polypeptide has a molecular weight of less than 150 kDa, more preferably less than 100 kDa, and more preferably less than 50 kDa. In one embodiment, the active agent is an active polypeptide, e.g., a therapeutic or prophylactic polypeptide and the polypeptide has a molecular weight of about 500 Da-5 kDa, 5 to 10 kDa, 10 to 30 kDa, 18-35 kDa, 30 to 50 kDa, 50 to 100 kDa, 100 to 150 kDa. In one embodiment, the active polypeptide is insulin or an active fragments or derivatives thereof. In another embodiment, the active polypeptide is human growth hormone or an active fragment or derivative thereof. In yet another embodiment, the active polypeptide is interferon or an active agent or derivative thereof. In another embodiment, the formulation further includes an inactive agent, e.g., an inactive agent described herein.

In another embodiment, the formulation further includes an active agent and the active agents can be a small molecule drug, e.g., a small drug currently available for therapeutic, diagnostic, or prophylactic use, and/or a drug in development. In some embodiments, the active agent is admixed with the polysaccharide. Admixtures can be prepared, e.g., by mixing, covalently-linked polysaccharides, ionically-linked polysaccharides, spraying drying and other techniques known in the art. In other embodiments, the active agent is linked to one or more polysaccharide in the formulation. As an example, small molecule drugs, and protein-based drugs may be linked to polysaccharides for delivery via known chemistries such as EDC, $CNBH_4$/DMSO/Acetic Acid, etc.

In some embodiments, the formulation is a dry formulation. In some embodiments, the dry formulation includes polysaccharide particles having a mean geometric diameter of 1 to 500 microns, e.g., particles having a mean geometric diameter of at least 2, 3, 4, 5, 10, 15, 20, 25, 30, 35, 40, 45, 50 or 100 microns. In other embodiments, the formulation is a liquid formulation, aerosol, mist, or a suspension. In some embodiments, the formulation further includes one or more delivery enhancer, e.g., one or more of a surfactant, an absorption enhancer, a protease inhibitor, etc.

In some embodiments, the formulation is provided in a device for pulmonary delivery, e.g., a pressurized or non-pressurized container or dispenser, e.g., a pressurized contained or dispenser which contains a suitable propellant and/or nebulizer, or is user activated. In one embodiment, the formulation is provided in a delivery device for pulmonary delivery that delivers a metered dose of the formulation to a subject.

In another aspect, the invention features a heparin, preferrably a LMWH, having one or more of the modifications described below. In a preferred embodiment the polysaccharide is a LMWH and is chosen from the group of: enoxaparin, dalteparin, reviparin, tinzaparin, nadroparin, certoparin, ardeparin, and pamaparin.

In some embodiments, the heparin is modified from unfractionated or fractionated heparin (LMWH). In some embodiments, the heparin is modified from a fractionated heparin selected from the group consisting of: enoxaparin, dalteparin, reviparin, tinzaparin, nadroparin, certoparin, ardeparin, and parnaparin.

In one embodiment, the heparin consists of about two, three, four, five, six, seven, eight, nine, ten, eleven, twelve, thirteen, fourteen, fifteen, sixteen, seventeen, eighteen, nineteen or twenty disaccharides. It is particularly preferred that the polysaccharide is a hexasaccharide or larger, and even more preferrably, an octasaccharide or larger.

In one embodiment, the heparin is modified such that the size of the heparin is reduced as compared to a reference standard, e.g., a commercially available version of the heparin or a heparin from which the modified heparin is derived. The size of the heparin can be reduced, e.g., by at least 5%, 10%, 15%, 20%, 30%, 40%, 50%, 60%, 70% or more as compared to the reference standard. In one embodiment, the size of the provided heparin can be reduced, e.g., by digesting the heparin with at least one agent, e.g., an agent selected based upon the chemical signature of the heparin. For example, the agent can be an enzyme (e.g., an enzyme which is capable of cleaving the heparin at known locations in the heparin based upon its chemical signature) or a chemical (e.g., a chemical capable of cleaving the heparin at known locations in the heparin based upon its chemical signature) or combinations thereof. Examples of enzymes which can be used include heparin degradation enzymes, e.g., heparin lysase such as heparinase I, heparinase II, heparinase III, heparinase IV, heparanase, and functionally active fragments and variants thereof. Examples of chemicals which can be used include oxidative depolymerization with $H_2O_2$ or $Cu^+$ and $H_2O_2$, deaminative cleavage with isoamyl nitrite, or nitrous acid, β-eliminative cleavage with benzyl ester of heparin by alkaline treatment or by heparinase. Other examples include chemicals for selective functional group changes: 2-O desulfonation by treatment with base, such as NaOH, and lyophilization; N-desulfonation with pyridine and DMSO; N+O desulfonation with pyridine and DMSO/dioxane/methanol; 6-O desulfonation with pyridine and NMP/$H_2O$; 3-O sulfonation with $SO_3$/trimethylamine/$H_2O$; and other approaches known in the art.

In another embodiment, the heparin is modified such that the charge of the heparin is modified, e.g., increased or decreased, as compared to a reference standard, e.g., a commercially available version of the heparin or a heparin from which the modified heparin is derived. Decreasing the charge of a heparin is also referred to herein as "neutralizing" the charge. In some embodiments, when the charge of the heparin is neutralized, the net negative or net positive charge of the heparin can be reduced by at least 10%, 20%, 30%, 40%, 50%, 60%, 70%, 80%, or 90%. In other embodiments, when the charge of the heparin is neutralized, it can be neutralized such that there is a net negative and net positive charge of 0. The heparin can be neutralized, e.g., by digesting the heparin with at least one agent, e.g., an agent selected based upon the chemical signature of the heparin. For example, the agent can be an enzyme (e.g., an enzyme which is capable of cleaving the heparin at known locations in the heparin based upon its chemical signature) or a chemical (e.g., a chemical capable of cleaving the heparin at known locations in the heparin based upon its chemical signature and/or a chemical providing a selective functional group modification) or combinations thereof. Examples of enzymes which can be used include heparin degradation enzymes, e.g., heparin lysase such as heparinase I, heparinase II, heparinase III, heparinase IV, heparanase, and functionally active fragments and variants thereof. Examples of chemicals which can be used include oxidative depolymerization with $H_2O_2$ or $Cu^+$ and $H_2O_2$, deaminative cleavage with isoamyl nitrite, or nitrous acid, β-eliminative cleavage with benzyl ester of heparin by alkaline treatment or by heparinase. Other examples include chemicals for selective functional group changes: 2-O desulfonation by treatment with base, such as NaOH and lyophilization; N-desulfonation with pyridine and DMSO; N+O desulfonation with pyridine and DMSO/dioxane/methanol; 6-O desulfonation with pyridine and NMP/$H_2O$; 3-O sulfonation with $SO_3$/trimethylamine/$H_2O$; and other approaches known in the art. In other embodiments, when the charge of the heparin is neutralized, it can be neutralized by contacting the heparin with a charge neutralizing agent, e.g., a counter ion such as mono- or divalent ion, (e.g., barium, calcium, sodium, potassium, lithium, ammonium, magnesium, zinc), a transition metal (e.g., iron, nickel and copper), and/or other neutralizing compounds (e.g., a small organic compound, spermine, spermidine, low molecular weight protamine, basic peptides).

In other embodiments, the net charge of the polysaccharide is increased, e.g., by increasing the charge density. The charge density can be increased, e.g., by removing one or more low charged domains, e.g., by the addition of one or more sulfate group, and/or other charged species, such as phosphates, acetates, etc. In some embodiments, sulfate groups and/or other charged species can be added by one or more of: enzymatic, chemical, or physical means.

In some embodiments, a chemical signature of the heparin from which the heparin is derived has been determined and the heparin is modified based upon its chemical signature. The chemical signature of the heparin can be used, e.g., to modify the heparin to reduce one or more therapeutic activities of the heparin, to modify the size and/or to modify the charge of the heparin. In other embodiments, a chemical signature of the heparin can been determined. Information regarding the chemical signature of a heparin can be used, e.g., to determine whether another polysaccharide is likely to have similar delivery properties as the heparin or to determine whether another polysaccharide is not likely to have similar delivery properties as the heparin.

In a preferred embodiment the heparin, e.g., a LMWH, is modified such that the anti-Xa activity and/or anti-IIa activity of the heparin is reduced by at least 30%, 40%, 50%, 60%, 70%, 80%, 90%, 95%, 99% or more as compared to a reference standard. In one embodiment, the anti-Xa activity and/or anti-IIa activity can be reduced by reducing the molecular weight (e.g., size) and/or by changes in functional group decoration. In some embodiments, the reference standard is the level of anti-Xa activity and/or anti-IIa activity of a commercially available version of the heparin or is the level of anti-Xa activity and/or anti-IIa activity of the heparin prior to modification.

In another aspect, the invention features a formulation for pulmonary delivery of a therapeutic, diagnostic, or prophylactic agent. The formulation includes a heparin, preferrably a LMWH, e.g., a heparin, e.g., LMWH described herein, and an active agent, e.g., a therapeutic, diagnostic or prophylactic agent. In a preferred embodiment the polysaccharide is a LMWH and is chosen from the group of: enoxaparin, dalteparin, reviparin, tinzaparin, nadroparin, certoparin, ardeparin, and pamaparin.

Therapeutic and prophylactic agents include a therapeutic or prophylactic polypeptide, nucleic acid, small molecule, lipid/glycolipids, etc. In one embodiment, the active agent is a therapeutic polypeptide selected from the group consisting of insulin, proinsulin, human growth hormone, interferon, α-1 proteinase inhibitor, alkaline phosphotase, angiogenin, cystic fibrosis transmembrane conductance regulator, extracellular superoxide dismutase, fibrinogen, glucocerebrosidase, glutamate decarboxylase, human serum albumin, myelin basic protein, soluble CD4, lactoferrin, lactoglobulin, lysozyme, lactoalbumin, erythropoietin, tissue plasminogen activator, antithrombin III, prolactin, and α1-antitrypsin. The therapeutic or prophylactic polypeptide can be an active derivative or fragment of such polypeptides. The active agent can also be, but is not limited to one or more of: parathyroid hormone and derivatives and fragments thereof, erythropoietin, epoetin beta, gene activated erythropoietin, second generation EPO, novel erythropoiesis stimulating protein, insulin lispro, insulin (bovine), insulin, insulin aspart, insulin analogue, Calcitonin, Theraccine, becaplermin (recombinant human platelet derived growth factor-BB), trafermin, human growth hormone-releasing factor, BMP-7, PEG aspariginase, domase alpha, alglucerase, agalsidase-beta, domase alpha, agalsidase-alfa, streptokinase, teneteplase, reteplase, alteplase, pamiteplase, Rh factor VIII, Rh FVIIa, Factor IX (Human), Factor IX (complex), HGH, Somatrem/somatropin, anti-CD33-calicheamicin conjugate, Edrecolomab, rituxumab, daclizumab, trastuzumab, sulesomab, abciximab, infliximab, muromonab-CD3, palivizumab, alemtuzumab, basiliximab, oprelvekin, gemtuzumab ozogamicin, ibritumomab tiuxetan, sulesomab, palivizumab, interleukin-2, celmoleukin (rIL-2), interferon alfacon-1, interferon alpha, interferon alpha+ribavirin, peg interferon alpha-2a, interferon alpha-2b, interferon alpha 3n, interferon beta-1a, interferon beta, interferon beta 1b, interferon gamma, interferon gamma-1b, filgrastim, sargramostim, lenograstim, molgramostim, mirimostim, nartograstim, oprelvekin, peptide tyrosin-tyrosin (PYY), apolipoprotein A-IV, leptin, melanocortin, amylin, orexin, adiponectin, and ghrelin. Other polypeptides, collectively "adipokines", are those implicated in regulating satiety, including peptide tyrosine-tyrosine (PYY), apolipoprotein A-IV, leptin, melanocortin, amylin, orexin, adiponectin and ghrelin. In one embodiment, the active agent is an active polypeptide, e.g., a therapeutic or prophylactic polypeptide, and the polypeptide has a molecular weight of less than 150 kDa, more preferrably less than 100 kDa, and more preferrably less than 50 kDa. In one embodiment, the active agent is an active polypeptide, e.g., a therapeutic or prophylactic polypeptide, and the polypeptide has a molecular weight of about 500 Da-5 kDa, 5 to 10 kDa, 10 to 30 kDa, 18-35 kDa, 30 to 50 kDa, 50 to 100 kDa, 100 to 150 kDa. In one embodiment, the active polypeptide is insulin or an active fragments or derivatives thereof. In another embodiment, the active polypeptide is human growth hormone or an active fragment or derivative thereof. In yet another embodiment, the active polypeptide is interferon.

In another embodiment, the active agent can be a small molecule drug, e.g., a small molecule drug currently available for therapeutic, diagnostic, or prophylactic use, or a drug in development. In some embodiments, the active agent is admixed with the polysaccharide. Admixtures can be prepared, e.g., by mixing, covalently-linked polysaccharides, ionically-linked polysaccharides, spraying drying and other techniques known in the art. In other embodiments, the active agent is linked to one or more polysaccharide in the formulation. As an example, small molecule drugs, and protein-based drugs may be linked to polysaccharides for delivery via known chemistries such as EDC, $CNBH_4$/DMSO/Acetic Acid, etc.

In other embodiments, the formulation includes a heparin, e.g., a heparin described herein, and an inactive agent. Examples of inactive agents include biological probes or contrast agents for imaging.

In some embodiments, the heparin is one in which one or more chemical signatures of a oligosaccharide of the heparin that include the structure: $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$, is modified to reduce the anti-Xa activity of the heparin, e.g., the heparin include one or more of $\Delta UH_{NAc,6S}GH_{NS,3S,6S}$ or $\Delta UH_{NAc,6S}GH_{NS,3S}$. In some embodiments, the heparin is M118, which has a molecular weight of 5,000 Da, a polydispersity of 1.0, and a higher weight percent of peak 8 than other LMWHs. M118 is a LMWH having XA and IIA activity on the same molecule and it is fully neutralizable by protamine.

In some embodiments, one or more monosaccharide or disaccharide is added or removed, and/or one or more acetyl group and/or sulfo group is substituted, removed or added, to modify the activity of the heparin.

In some embodiments, the formulation is a dry formulation. In some embodiments, the dry formulation includes heparin particles having a mean geometric diameter of 1 to 500 microns, e.g., particles having a mean geometric diameter of at least 2, 3, 4, 5, 10, 15, 20, 25, 30, 35, 40, 45, 50 or 100 microns. In other embodiments, the formulation is a liquid formulation (e.g., an aerosol, mist, or a suspension).

In some embodiments, the formulation further includes one or more delivery enhancers, e.g., one or more of a surfactant, an absorption enhancer, protease inhibitor, etc.

In some embodiments, the formulation is provided in a device for pulmonary delivery, e.g., a pressurized or non-pressurized container or dispenser, e.g., a pressurized contained or dispenser which contains a suitable propellant and/or nebulizer, or is user activated. In one embodiment, the formulation is provided in a delivery device for pulmonary delivery that delivers a metered dose of the formulation to a subject.

In another aspect, the invention features a formulation for pulmonary delivery of a therapeutic or prophylactic agent that includes a heterogeneous population of heparin, preferably of LMWH, wherein the population is modified such that anti-Xa activity and/or anti-IIa activity of the population of heparin is reduced by at least 30%, 40%, 50%, 60%, 70%, 80%, 90%, 95%, 99% or more as compared to a reference standard. In some embodiments, the reference standard is the level of therapeutic activity of a commercially available version of the heparin population or is the level of therapeutic activity of the heparin population prior to modification. In one embodiment, the heterogeneous population of heparin is a population of heparin as described herein.

In one embodiment, all or a portion of heparin of the population consist of about two, three, four, five, six, seven, eight, nine, ten, eleven, twelve, thirteen, fourteen, fifteen, sixteen, seventeen, eighteen, nineteen or twenty disaccharides. It is particularly preferred that the polysaccharide is an hexasaccharide or larger, and even more preferrably, an octasaccharide or larger.

In one embodiment, the heparin population is modified such that the size of all or a portion of the heparin is reduced as compared to a reference standard, e.g., a commercially available version of the heparin population or a heparin population from which the modified heparin is derived. The size all or a portion of the heparin can be reduced, e.g., by at least 5%, 10%, 15%, 20%, 30%, 40%, 50%, 60%, 70% or more as compared to the reference standard. In one embodiment, the size of all or a portion of the provided heparin population can be reduced, e.g., by digesting the heparin with at least one agent, e.g., an agent selected based upon the chemical signature of one or more of the heparins of the population. For example, the agent can be an enzyme (e.g., an enzyme which is capable of cleaving heparin at known locations in the heparin based upon its chemical signature) or a chemical (e.g., a chemical capable of cleaving heparins at known locations in the heparin based upon its chemical signature) or combinations thereof. Examples of enzymes which can be used include heparin degradation enzymes, e.g., heparin lysase such as heparinase I, heparinase II, heparinase III, heparinase IV, heparanase, and functionally active fragments and variants thereof. Examples of chemicals which can be used include oxidative depolymerization with $H_2O_2$ or $Cu^+$ and $H_2O_2$, deaminative cleavage with isoamyl nitrite, or nitrous acid, β-eliminative cleavage with benzyl ester of heparin by alkaline treatment or by heparinase. Other examples include chemicals for selective functional group changes: 2-O desulfonation by treatment with base, such as NaOH and lyophilization; N-desulfonation with pyridine and DMSO; N+O desulfonation with pyridine and DMSO/dioxane/methanol; 6-O desulfonation with pyridine and NMP/$H_2O$; 3-O sulfonation with $SO_3$/trimethylamine/$H_2O$; and other approaches known in the art.

In another embodiment, the population of heparin is modified such that the charge of all or a portion of the heparin is modified, e.g., increased or decreased, as compared to a reference standard, e.g., a commercially available version of the heparin population or a heparin population from which the modified heparin is derived. Decreasing the charge of a heparin is also referred to herein as "neutralizing" the charge. In some embodiments, when the charge of the heparin is neutralized, the net negative or net positive charge of the heparin can be reduced by at least 10%, 20%, 30%, 40%, 50%, 60%, 70%, 80%, or 90%. In other embodiments, when the charge of the heparin is neutralized, it can be neutralized such that there is a net negative and net positive charge of 0. All or a portion of the heparin population can be neutralized, e.g., by digesting the heparin population with at least one agent, e.g., an agent selected based upon the chemical signature of one or more of the heparins in the population. For example, the agent can be an enzyme (e.g., an enzyme which is capable of cleaving heparin at known locations in the heparin based upon its chemical signature) or a chemical (e.g., a chemical capable of cleaving heparin at known locations in the heparin based upon its chemical signature and/or a chemical providing selective functional group modification) or combinations thereof. Examples of enzymes which can be used include heparin degradation enzymes, e.g., heparin lysase such as heparinase I, heparinase II, heparinase III, heparinase IV, heparanase, and functionally active fragments and variants thereof. Examples of chemicals which can be used include oxidative depolymerization with $H_2O_2$ or $Cu^+$ and $H_2O_2$, deaminative cleavage with isoamyl nitrite, or nitrous acid, β-eliminative cleavage with benzyl ester of heparin by alkaline treatment or by heparinase. Other examples include chemicals for selective functional group changes: 2-O desulfonation by treatment with base, such as NaOH and lyophilization; N-desulfonation with pyridine and DMSO; N+O desulfonation with pyridine and DMSO/dioxane/methanol; 6-O desulfonation with pyridine and NMP/$H_2O$; 3-O sulfonation with $SO_3$/trimethylamine/$H_2O$; and other approaches known in the art. In other embodiments, when the charge of one or more heparins of the population is neutralized, it can be neutralized by contacting the heparin population with a charge neutralizing agent, e.g., a counter ion such as mono- or divalent ion, (e.g., barium, calcium, sodium, potassium, lithium, ammonium, magnesium, zinc), a transition metal (e.g., iron, nickel and copper), and/or other neutralizing compounds (e.g., a small organic compound, spermine, spermidine, low molecular weight protamine, basic peptides).

In other embodiments, the net charge of the heparin is increased, e.g., by increasing the charge density. The charge density can be increased, e.g., by removing one or more low charged domains, e.g., by the addition of one or more sulfate group, and/or other charged species, such as phosphates, acetates, etc. In some embodiments, sulfate groups and/or other charged species can be added by one or more of: enzymatic, chemical, or physical means.

In some embodiments, a chemical signature of one or more of the heparins of the population from which the heparin is derived has been determined and the heparin is modified based upon its chemical signature. The chemical signature of the heparin can be used, e.g., to modify the heparin to reduce one or more therapeutic activities of the heparin population, to modify the size and/or to modify the charge of one or more heparin chain in the population. In other embodiments, a chemical signature of one or more of the heparin can been determined. Information regarding the chemical signature of a heparin can be used, e.g., to determine whether another polysaccharide is likely to have similar delivery properties as the heparin or to determine whether another polysaccharide is not likely to have similar delivery properties as the heparin. In some embodiments, the chemical signature of the heparin is compared to a chemical signature of a polysaccharide involved in lung activity, e.g., normal physiology and/or homeostasis of the lung. The invention can further include modifying the heparin based upon similarities and/or differences between the chemical signature of the polysaccharide and the polysaccharide or polysaccharides involved in lung activity.

In some embodiments, the formulation further includes an active agent, e.g., a therapeutic, diagnostic or prophylactic agent. Therapeutic and prophylactic agents include therapeutic or prophylactic polypeptides, nucleic acids, small molecule, lipid/glycolipids, etc. In one embodiment, the active agent is a therapeutic polypeptide selected from the group consisting of insulin, proinsulin, human growth hormone, interferon, α-1 proteinase inhibitor, alkaline phosphotase, angiogenin, cystic fibrosis transmembrane conductance regulator, extracellular superoxide dismutase, fibrinogen, glucocerebrosidase, glutamate decarboxylase, human serum albumin, myelin basic protein, soluble CD4, lactoferrin, lactoglobulin, lysozyme, lactoalbumin, erythropoietin, tissue plasminogen activator, antithrombin III, prolactin, and α1-antitrypsin. In another embodiment, the active agent can be one or more of: parathyroid hormone and derivatives and fragments thereof, erythropoietin, epoetin beta, gene activated erythropoietin, epoetin beta, second generation EPO, epoetin beta, novel erythropoiesis stimulating protein, insulin lispro, insulin (bovine), insulin, insulin aspart, Insulin analogue, Calcitonin, Theraccine, becaplermin (recombinant human platelet derived growth factor-BB), trafermin, human growth hormone-releasing factor, BMP-7, PEG aspariginase, domase alpha, alglucerase, agalsidase-beta, domase alpha, agalsidase-alfa, streptokinase, teneteplase, reteplase, alteplase, pamiteplase, Rh factor VIII, Rh FVIIa, Factor IX (Human), Factor IX (complex), HGH, Somatrem/somatropin, anti-CD33-calicheamicin conjugate, Edrecolomab, rituxumab, trastuzumab, daclizumab, sulesomab, abciximab, infliximab, muromonab-CD3, palivizumab, alemtuzumab, basiliximab, oprelvekin, gemtuzumab ozogamicin, ibritumomab tiuxetan, sulesomab, palivizumab, interleukin-2, celmoleukin (rIL-2), interferon alfacon-1, interferon alpha, interferon alpha+ribavirin, PEG interferon alpha-2a, interferon alpha-2b, interferon alpha 3n, interferon beta-1a, interferon beta, interferon beta 1b, interferon gamma, interferon gamma-1b, filgrastim, lenograstim, sargramostim, molgramostim, mirimostim, sargramostim, nartograstim, oprelvekin, peptide tyrosin-tyrosin (PYY), apolipoprotein A-IV, leptin, melanocortin, amylin, orexin, adiponectin, and ghrelin. Other polypeptides, collectively "adipokines", are those implicated in regulating satiety, including peptide tyrosine-tyrosine (PYY), apolipoprotein A-IV, leptin, melanocortin, amylin, orexin, adiponectin and ghrelin. The therapeutic or prophylactic polypeptide can be an active derivative or fragment of such polypeptides. In one embodiment, the active agent is an active polypeptide, e.g., a therapeutic or prophylactic polypeptide, and the polypeptide has a molecular weight of less than 150 kDa, more preferrably less than 100 kDa, and more preferrably less than 50 kDa. In one embodiment, the active agent is an active polypeptide, e.g., a therapeutic or prophylactic polypeptide and the polypeptide has a molecular weight of about 500 Da-5 kDa, 5 to 10 kDa, 10 to 30 kDa, 18 to 35 kDa, 30 to 50 kDa, 50 to 100 kDa, 100 to 150 kDa. In one embodiment, the active polypeptide is insulin or an active fragments or derivatives thereof. In another embodiment, the active polypeptide is human growth hormone or an active fragment or derivative thereof. In yet another embodiment, the active polypeptide is interferon or active fragment or derivative thereof.

In some embodiments, the active agent is admixed with the polysaccharide. Admixtures can be prepared, e.g., by mixing, covalently-linked polysaccharides, ionically-linked polysaccharides, spraying drying and other techniques known in the art. In other embodiments, the active agent is linked to one or more polysaccharide in the formulation. As an example, small molecule drugs, and protein-based drugs may be linked to polysaccharides for delivery via known chemistries such as EDC, $CNBH_4$/DMSO/Acetic Acid, etc.

In other embodiments, the formulation includes an inactive agent. Examples of inactive agents include biological probes or contrast agents for imaging.

In some embodiments, the formulation is a dry formulation. In some embodiments, the dry formulation includes heparin particles having a mean geometric diameter of 1 to 500 microns, e.g., particles having a mean geometric diameter of at least 2, 3, 4, 5, 10, 15, 20, 25, 30, 35, 40, 45, 50 or 100 microns. In other embodiments, the formulation is a liquid formulation, aerosol, mist, or a suspension.

In some embodiments, the formulation further includes one or more delivery enhancer, e.g., one or more surfactant, absorption enhancer, protease inhibitor, etc.

In some embodiments, the formulation is provided in a device for pulmonary delivery, e.g., a pressurized or non-pressurized container or dispenser, e.g., a pressurized contained or dispenser which contains a suitable propellant and/or nebulizer, or is user activated. In one embodiment, the formulation is provided in a delivery device for pulmonary delivery that delivers a metered dose of the formulation to a subject.

In some embodiments, all or some of the heparin are in which one or more chemical signatures of a oligosaccharide of the heparin includes the structure: $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$, that is modified to reduce the anti-Xa activity of all or some of the heparin, for example, the heparin includes the structure of at least one of $\Delta UH_{NAc,6S}GH_{NS,3S,6S}$ or $\Delta UH_{NAc,6S}GH_{NS,3S}$. In some embodiments, the heparin is M118, which has a molecular weight of 5,000 Da, a polydispersity of 1.0, and a higher weight percent of peak 8 than other LMWHs.

In some embodiments, one or more monosaccharide or disaccharide is added or removed, and/or one or more acetyl group and/or sulfo group is substituted, removed or added, to modify the activity of the heparin.

In another aspect, the invention features a method of making a polysaccharide, e.g., an HLGAG, e.g., heparin or a LMWH, e.g., such as described herein, for pulmonary delivery of an active agent, e.g., a therapeutic or prophylactic agent. The method includes: providing a polysaccharide, e.g., a heparin or a LMWH, and modifying it in one or more of the ways described herein.

In a preferred embodiment the polysaccharide is a LMWH and is chosen from the group of: enoxaparin, dalteparin, reviparin, tinzaparin, nadroparin, certoparin, ardeparin, and parnaparin.

In some embodiments, the method includes modifying one or more of the structures: $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$, of the heparin to reduce the anti-Xa activity of the heparin, e.g., a LMWH. In some embodiments, the heparin includes the structure of at least one of $\Delta UH_{NAc,6S}GH_{NS,3S,6S}$ or $\Delta UH_{NAc,6S}GH_{NS,3S}$. In some embodiments, the heparin is M118, which has a molecular weight of 5,000 Da, a polydispersity of 1.0, and a higher weight percent of peak 8 than other LMWHs.

In some embodiments, one or more monosaccharide or disaccharide is added or removed, and/or one or more acetyl group and/or sulfo group is substituted, removed or added, to modify the activity of the heparin.

In some embodiments, the heparin, e.g., a LMWH, is modified from unfractionated or fractionated heparin. In some embodiments, the heparin is modified from a fractionated heparin selected from the group consisting of: enoxaparin, dalteparin, reviparin, tinzaparin, nadroparin, certoparin, ardeparin, and parnaparin. In some embodiments, the heparin is modified based upon similarities and/or differences between the chemical signature of the heparin and a polysaccharide or polysaccharides involved in lung activity.

In one embodiment, the modified heparin, e.g., a LMWH, consists of about two, three, four, five, six, seven, eight, nine, ten, eleven, twelve, thirteen, fourteen, fifteen, sixteen, seventeen, eighteen, nineteen or twenty disaccharides. It is particularly preferred that the polysaccharide is a hexasaccharide or larger, and even more preferrably, an octasaccharide or larger.

In one embodiment, the heparin, e.g., a LMWH, is modified such that the size of the heparin, e.g., a LMWH, is reduced as compared to a reference standard, e.g., a commercially available version of the heparin or a heparin from which the modified heparin, e.g., a LMWH, is derived. The size of the heparin, e.g., a LMWH, can be reduced, e.g., by at least 5%, 10%, 15%, 20%, 30%, 40%, 50%, 60%, 70% or more as compared to the reference standard. In another embodiment, the heparin, e.g., a LMWH, is modified such that the charge of the heparin is modified, e.g., increased or decreased, as compared to a reference standard, e.g., a commercially available version of the heparin or a heparin from which the modified heparin, e.g., a LMWH, is derived. Decreasing the charge of a heparin, e.g., a LMWH, is also referred to herein as "neutralizing" the charge. In some embodiments, when the charge of the heparin is neutralized, the net negative or net positive charge of the heparin can be reduced by at least 10%, 20%, 30%, 40%, 50%, 60%, 70%, 80%, or 90%. In other embodiments, when the charge of the heparin is neutralized, it can be neutralized such that there is a net negative and net positive charge of 0.

In another embodiment, the method further includes modifying the size of the heparin such that it is reduced as compared to the reference standard. In one embodiment, the size of the provided heparin can be reduced, e.g., by a method described herein.

In another embodiment, the method includes modifying the charge of the heparin such that the charge of the heparin is modified, e.g., increased or decreased, as compared to a reference standard, e.g., a commercially available version of the heparin or a heparin from which the modified heparin is derived. In one embodiment, the charge of the heparin can be decreased or neutralized, e.g., by a method described herein. In other embodiments, the net charge of the polysaccharide is increased, e.g., by a method described herein.

In some embodiments, the method further includes determining the chemical signature of the heparin from which the heparin is derived and modifying the heparin based upon its chemical signature. The chemical signature of the heparin can be used, e.g., to modify the heparin to reduce one or more therapeutic activities of the heparin, to modify the size and/or to modify the charge of the heparin. In other embodiments, the method further includes determining the chemical signature of the heparin and using the chemical signature, e.g., to determine whether another polysaccharide is likely to have similar delivery properties as the heparin or to determine whether another polysaccharide is not likely to have similar delivery properties as the heparin. In some embodiments, the chemical signature of the heparin is compared to a chemical signature of a polysaccharide involved in lung activity, e.g., normal physiology and/or homeostasis of the lung. The invention can include modifying the heparin based upon similarities and/or differences between the chemical signature of the heparin and the polysaccharide or polysaccharides involved in lung activity.

In a preferred embodiment the polysaccharide is modified such that anti-Xa activity and/or anti-IIa activity is reduced by at least 30%, 40%, 50%, 60%, 70%, 80%, 90%, 95%, 99% or more than a reference standard, to thereby provide a heparin. In some embodiments, the reference standard is the level of anti-Xa activity and/or anti-IIa activity of a commercially available version of the heparin or is the level of anti-Xa activity and/or anti-IIa of the heparin prior modification.

In one embodiment, the method further includes combining the heparin with an active agent, e.g., a therapeutic or prophylactic agent. The heparin can be combined, e.g., with a therapeutic or prophylactic agent is selected from the group consisting of: a polypeptide, a nucleic acid, a small molecule, a lipid, and a glycolipid.

In one embodiment, the heparin is combined with a therapeutic or prophylactic polypeptide selected from the group consisting of: insulin, proinsulin, human growth hormone, interferon, α-1 proteinase inhibitor, alkaline phosphotase, angiogenin, cystic fibrosis transmembrane conductance regulator, extracellular superoxide dismutase, fibrinogen, glucocerebrosidase, glutamate decarboxylase, human serum albumin, myelin basic protein, soluble CD4, lactoferrin, lactoglobulin, lysozyme, lactoalbumin, erythropoietin, tissue plasminogen activator, antithrombin III, prolactin, and α1-antitrypsin. In another embodiment, the heparin is combined with the therapeutic or prophylactic agent selected from the group consisting of: parathyroid hormone and derivatives and fragments thereof, erythropoietin, epoetin beta, gene activated erythropoietin, epoetin beta, second generation EPO, epoetin beta, novel erythropoiesis stimulating protein, insulin lispro, insulin (bovine), insulin, insulin aspart, insulin analogue, Calcitonin, Theraccine, becaplermin (recombinant human platelet derived growth factor-BB), trafermin, human growth hormone-releasing factor, BMP-7, PEG aspariginase, domase alpha, alglucerase, agalsidase-beta, domase alpha, agalsidase-alfa, streptokinase, teneteplase, reteplase, alteplase, pamiteplase, Rh factor VIII, Rh FVIIa, Factor IX (Human), Factor IX (complex), HGH, Somatrem/somatropin, Anti-CD33-calicheamicin conjugate, Edrecolomab, rituxumab, daclizumab, trastuzumab, sulesomab, abciximab, infliximab, muromonab-CD3, palivizumab, alemtuzumab, basiliximab, oprelvekin, gemtuzumab ozogamicin, ibritumomab tiuxetan, sulesomab, palivizumab, interleukin-2, celmoleukin (rIL-2), interferon alfacon-1, interferon alpha, interferon alpha+ribavirin, peg interferon alpha-2a, interferon alpha-2b, interferon alpha 3n, interferon beta-1a, interferon beta, interferon beta 1b, interferon gamma, interferon gamma-1b, filgrastim, lenograstim, sargramostim, molgramostim, mirimostim, sargramostim, nartograstim, oprelvekin, peptide tyrosin-tyrosin (PYY), apolipoprotein A-IV, leptin, melanocortin, amylin, orexin, adiponectin, and ghrelin. Other polypeptides, collectively "adipokines", are those implicated in regulating satiety, including peptide tyrosine-tyrosine (PYY), apolipoprotein A-IV, leptin, melanocortin, amylin, orexin, adiponectin and ghrelin. The therapeutic or prophylactic polypeptide can be an active derivative or fragment of such polypeptides. In one embodiment, the active agent is an active polypeptide, e.g., a therapeutic or prophylactic polypeptide, and the polypeptide has a molecular weight of less than 150 kDa, more preferrably less than 100 kDa, and more preferrably less than 50 kDa. In one embodiment, the active agent is an active polypeptide, e.g., a therapeutic or prophylactic polypeptide and the polypeptide has a molecular weight of about 500 Da-5 kDa, 5 to 10 kDa, 10 to 30 kDa, 18 to 35 kDa, 30 to 50 kDa, 50 to 100 kDa, 100 to 150 kDa. In one embodiment, the active polypeptide is insulin or an active fragments or derivatives thereof. In another embodiment, the active polypeptide is human growth hormone or an active fragment or derivative thereof. In yet another embodiment, the active polypeptide is interferon or active fragment or derivative thereof.

In one embodiment, the heparin is combined with the therapeutic or prophylactic agent by admixing the heparin and the therapeutic or prophylactic agent. Admixtures can be prepared, e.g., by mixing, covalently-linked polysaccharides, ionically-linked polysaccharides, spraying drying and other techniques known in the art. In other embodiments, the heparin is combined with the therapeutic or prophylactic agent by linking the heparin and the therapeutic or prophylactic agent. As an example, small molecule drugs, and protein-based drugs may be linked to polysaccharides for delivery via known chemistries such as EDC, $CNBH_4$/DMSO/Acetic Acid, etc. In some embodiments, the formulation is provided in a device for pulmonary delivery, e.g., a pressurized or non-pressurized container or dispenser, e.g., a pressurized contained or dispenser which contains a suitable propellant and/or nebulizer, or is user activated. In one embodiment, the formulation is provided in a delivery device for pulmonary delivery that delivers a metered dose of the formulation to a subject.

In another aspect, the invention features a method of preparing a formulation for pulmonary delivery of an active agent, e.g., a therapeutic or prophylactic agent. The method includes: combining an active agent, e.g., an active agent described herein, and a polysaccharide, e.g., a HLGAG, e.g., heparin, e.g., a LMWH, e.g., such as described herein, to thereby prepare a formulation for pulmonary delivery of the therapeutic or prophylactic agent. In a preferred embodiment the polysaccharide is a LMWH and is chosen from the group of: enoxaparin, dalteparin, reviparin, tinzaparin, nadroparin, certoparin, ardeparin, and pamaparin.

In some embodiments, the heparin is modified from unfractionated or fractionated heparin (LMWH). In some embodiments, the heparin is modified from a fractionated heparin selected from the group consisting of: enoxaparin, dalteparin, reviparin, tinzaparin, nadroparin, certoparin, ardeparin, and pamaparin. In some embodiments, the heparin is a heparin described herein.

In some embodiments, the heparin is in a heterogeneous population of molecules, and, e.g., all or some of the molecules in the population are heparin, e.g., as described herein.

In some embodiments, the method includes combining the heparin, e.g., a heparin described herein, with a therapeutic or prophylactic agents from the group consisting of: therapeutic or prophylactic polypeptides, nucleic acids, small molecule, lipid/glycolipids, etc. In one embodiment, the heparin, e.g., a heparin described herein is combined with a therapeutic polypeptide selected from the group consisting of: insulin, proinsulin, human growth hormone, interferon, α-1 proteinase inhibitor, alkaline phosphotase, angiogenin, cystic fibrosis transmembrane conductance regulator, extracellular superoxide dismutase, fibrogen, glucocerebrosidase, glutamate decarboxylase, human serum albumin, myelin basic protein, soluble CD4, lactoferrin, lactoglobulin, lysozyme, lactoalbumin, erythropoietin, tissue plasminogen activator, antithrombin III, prolactin, and α1-antitrypsin. In another embodiment, the method includes combining the heparin, e.g., a heparin described herein, with one or more active agent from the group consisting of: parathyroid hormone and derivatives and fragments thereof, erythropoietin, epoetin beta, gene activated erythropoietin, epoetin beta, second generation EPO, epoetin beta, novel erythropoiesis stimulating protein, insulin lispro, insulin (bovine), insulin, insulin aspart, insulin analogue, Calcitonin, Theraccine, becaplermin (recombinant human platelet derived growth factor-BB), trafermin, human growth hormone-releasing factor, BMP-7, PEG aspariginase, domase alpha, alglucerase, agalsidase-beta, domase alpha, agalsidase-alfa, streptokinase, teneteplase, reteplase, alteplase, pamiteplase, Rh factor VIII, Rh FVIIa, Factor IX (Human), Factor IX (complex), HGH, Somatrem/somatropin, anti-CD33-calicheamicin conjugate, Edrecolomab, rituxumab, trastuzumab, daclizumab, sulesomab, abciximab, infliximab, muromonab-CD3, palivizumab, alemtuzumab, basiliximab, oprelvekin, gemtuzumab ozogamicin, ibritumomab tiuxetan, sulesomab, palivizumab, interleukin-2, celmoleukin (rIL-2), interferon alfacon-1, interferon alpha, interferon alpha+ribavirin, PEG interferon alpha-2a, interferon alpha-2b, interferon alpha 3n, interferon beta-1a, interferon beta, interferon beta 1b, interferon gamma, interferon gamma-1b, filgrastim, lenograstim, sargramostim, molgramostim, mirimostim, sargramostim, nartograstim, oprelvekin, peptide tyrosin-tyrosin (PYY), apolipoprotein A-IV, leptin, melanocortin, amylin, orexin, adiponectin, and ghrelin. Other polypeptides, collectively "adipokines", are those implicated in regulating satiety, including peptide tyrosine-tyrosine (PYY), apolipoprotein A-IV, leptin, melanocortin, amylin, orexin, adiponectin and ghrelin. The therapeutic or prophylactic polypeptide can be an active derivative or fragment of such polypeptides. In one embodiment, the active agent is an active polypeptide, e.g., a therapeutic or prophylactic polypeptide, and the polypeptide has a molecular weight of less than 150 kDa, more preferrably less than 100 kDa, and more preferrably less than 50 kDa. In one embodiment, the heparin is combined with an active agent and the active agent is an active polypeptide, e.g., a therapeutic or prophylactic polypeptide and the polypeptide has a molecular weight of about 500 Da-5 kDa, 5 to 10 kDa, 10 to 30 kDa, 18 to 35 kDa, 30 to 50 kDa, 50 to 100 kDa, 100 to 150 kDa. In one embodiment, the active polypeptide is insulin or an active fragments or derivatives thereof. In another embodiment, the active polypeptide is human growth hormone or an active fragment or derivative thereof. In yet another embodiment, the active polypeptide is interferon or active fragment or derivative thereof.

In some embodiments, the active agent is combined with the heparin by admixing the active agent with the heparin. Admixtures can be prepared, e.g., by mixing, covalently-linked polysaccharides, ionically-linked polysaccharides, spraying drying and other techniques known in the art. In other embodiments, the active agent is combined with the heparin by linking the active agent to one or more heparin in the formulation. As an example, small molecule drugs, and protein-based drugs may be linked to polysaccharides for delivery via known chemistries such as EDC, $CNBH_4$/DMSO/Acetic Acid, etc.

In some embodiments, the formulation is a dry formulation. In some embodiments, the dry formulation includes heparin particles having a mean geometric diameter of 1 to 500 microns, e.g., particles having a mean geometric diameter of at least 2, 3, 4, 5, 10, 15, 20, 25, 30, 35, 40, 45, 50 or 100 microns. In other embodiments, the formulation is a liquid formulation, aerosol, mist, or a suspension.

In some embodiments, the method further includes adding one or more delivery enhancer, e.g., one or more surfactant, absorption enhancer, protease inhibitor, etc., to the formulation.

In some embodiments, the method further includes providing and/or packaging the formulation in a device for pulmonary delivery, e.g., a pressurized or non-pressurized container or dispenser, e.g., a pressurized contained or dispenser which contains a suitable propellant and/or nebulizer, or is user activated. In one embodiment, the formulation is provided in a delivery device for pulmonary delivery that delivers a metered dose of the formulation to a subject.

In another aspect, the invention features a method of delivering a therapeutic or prophylactic agent to a subject. The method includes: administering to the pulmonary tissue of a subject a composition that includes an effective amount of a therapeutic or prophylactic agent and a polysaccharide, such as described herein.

In a preferred embodiment the polysaccharide is a LMWH and is chosen from the group of: enoxaparin, dalteparin, reviparin, tinzaparin, nadroparin, certoparin, ardeparin, and pamaparin.

In some embodiments, the heparin is modified from unfractionated or fractionated heparin (LMWH). In some embodiments, the heparin is modified from a fractionated heparin selected from the group consisting of: enoxaparin, dalteparin, reviparin, tinzaparin, nadroparin, certoparin, ardeparin, and pamaparin.

In one embodiment, the heparin consists of about two, three, four, five, six, seven, eight, nine, ten, eleven, twelve, thirteen, fourteen, fifteen, sixteen, seventeen, eighteen, nineteen or twenty disaccharides. It is particularly preferred that the polysaccharide is a hexasaccharide or larger, and even more preferrably, an octasaccharide or larger.

In one embodiment, the heparin is modified such that the size of the heparin is reduced as compared to a reference standard, e.g., a commercially available version of the heparin or a heparin from which the modified heparin is derived. The size of the heparin can be reduced, e.g., by at least 5%, 10%, 15%, 20%, 30%, 40%, 50%, 60%, 70% or more as compared to the reference standard. In one embodiment, the size of the provided heparin can be reduced, e.g., by a method described herein.

In another embodiment, the heparin is modified such that the charge of the heparin is modified, e.g., increased or decreased, as compared to a reference standard, e.g., a commercially available version of the heparin or a heparin from which the modified heparin is derived. Decreasing the charge of a heparin is also referred to herein as "neutralizing" the charge. In some embodiments, when the charge of the heparin is neutralized, the net negative or net positive charge of the heparin can be reduced by at least 10%, 20%, 30%, 40%, 50%, 60%, 70%, 80%, or 90%. In other embodiments, when the charge of the heparin is neutralized, it can be neutralized such that there is a net negative and net positive charge of 0. The heparin can be neutralized, e.g., by a method described herein. In other embodiments, the net charge of the polysaccharide is increased, e.g., by a method described herein.

In a preferred embodiment the polysaccharide is modified such that it has an anti-Xa activity and/or anti-IIa activity that is reduced by at least 30%, 40%, 50%, 60%, 70%, 80%, 90%, 95%, 99% or more as compared to a reference standard, to thereby deliver the therapeutic or prophylactic agent to the subject. In one embodiment, the reference standard is the level of anti-Xa activity and/or anti-IIa activity of a commercially available version of the heparin or is the level of anti-Xa activity and/or anti-IIa activity of the heparin prior modification. In other embodiments, a heparin is selected based upon similarities between its chemical signature and the chemical signature of one or more polysaccharides involved in lung activity, e.g., normal physiology and/or homeostasis.

In some embodiments, the active agent, e.g., the therapeutic and prophylactic agents is a therapeutic or prophylactic polypeptide, nucleic acid, small molecule, lipid/glycolipids, etc. In one embodiment, the active agent is a therapeutic polypeptide selected from the group consisting of insulin, proinsulin, human growth hormone, interferon, α-1 proteinase inhibitor, alkaline phosphotase, angiogenin, cystic fibrosis transmembrane conductance regulator, extracellular superoxide dismutase, fibrinogen, glucocerebrosidase, glutamate decarboxylase, human serum albumin, myelin basic protein, soluble CD4, lactoferrin, lactoglobulin, lysozyme, lactoalbumin, erythropoietin, tissue plasminogen activator, antithrombin III, prolactin, and α1-antitrypsin. The therapeutic or prophylactic polypeptide can be an active derivative or fragment of such polypeptides. The active agent can also be, but is not limited to one or more of: parathyroid hormone and derivatives and fragments thereof, erythropoietin, epoetin beta, gene activated erythropoietin, second generation EPO, novel erythropoiesis stimulating protein, insulin lispro, insulin (bovine), insulin, insulin aspart, insulin analogue, Calcitonin, Theraccine, becaplermin (recombinant human platelet derived growth factor-BB), trafermin, human growth hormone-releasing factor, BMP-7, PEG aspariginase, domase alpha, alglucerase, agalsidase-beta, dornase alpha, agalsidase-alfa, streptokinase, teneteplase, reteplase, alteplase, pamiteplase, Rh factor VIII, Rh FVIIa, Factor IX (Human), Factor IX (complex), HGH, Somatrem/somatropin, anti-CD33-calicheamicin conjugate, Edrecolomab, rituxumab, daclizumab, trastuzumab, sulesomab, abciximab, infliximab, muromonab-CD3, palivizumab, alemtuzumab, basiliximab, oprelvekin, gemtuzumab ozogamicin, ibritumomab tiuxetan, sulesomab, palivizumab, interleukin-2, celmoleukin (rIL-2), interferon alfacon-1, interferon alpha, interferon alpha+ribavirin, peg interferon alpha-2a, interferon alpha-2b, interferon alpha 3n, interferon beta-1a, interferon beta, interferon beta 1b, interferon gamma, interferon gamma-1b, filgrastim, sargramostim, lenograstim, molgramostim, mirimostim, nartograstim, oprelvekin, peptide tyrosin-tyrosin (PYY), apolipoprotein A-IV, leptin, melanocortin, amylin, orexin, adiponectin, and ghrelin. Other polypeptides, collectively "adipokines", are those implicated in regulating satiety, including peptide tyrosine-tyrosine (PYY), apolipoprotein A-IV, leptin, melanocortin, amylin, orexin, adiponectin and ghrelin. In one embodiment, the active agent is an active polypeptide, e.g., a therapeutic or prophylactic polypeptide, and the polypeptide has a molecular weight of less than 150 kDa, more preferrably less than 100 kDa, and more preferrably less than 50 kDa. In one embodiment, the active agent is an active polypeptide, e.g., a therapeutic or prophylactic polypeptide, and the polypeptide has a molecular weight of about 500 Da-5 kDa, 5 to 10 kDa, 10 to 30 kDa, 18 to 35 kDa, 30 to 50 kDa, 50 to 100 kDa, 100 to 150 kDa. In one embodiment, the active polypeptide is insulin or an active fragments or derivatives thereof. In another embodiment, the active polypeptide is human growth hormone or an active fragment or derivative thereof. In yet another embodiment, the active polypeptide is interferon.

In another embodiment, the active agent can be a small molecule drug, e.g., a small molecule drug currently available for therapeutic, diagnostic, or prophylactic use, or a drug in development. In some embodiments, the active agent is admixed with the polysaccharide. Admixtures can be prepared, e.g., by mixing, covalently-linked polysaccharides, ionically-linked polysaccharides, spraying drying and other techniques known in the art. In other embodiments, the active agent is linked to one or more polysaccharide in the formulation. As an example, small molecule drugs, and protein-based drugs may be linked to polysaccharides for delivery via known chemistries such as EDC, $CNBH_4$/DMSO/Acetic Acid, etc.

In other embodiments, the composition includes a heparin, e.g., a heparin described herein, and an inactive agent. Examples of inactive agents include biological probes or contrast agents for imaging.

In some embodiments, the heparin is one in which one or more chemical signatures of a oligosaccharide of the heparin that includes the structure: $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$, is modified to reduce the anti-Xa activity of the heparin, for example, the heparin includes the structure of at least one of $\Delta UH_{NAc,6S}GH_{NS,3S,6S}$ or $\Delta UH_{NAc,6S}GH_{NS,3S}$. In some embodiments, the heparin is M118, which has a molecular weight of 5,000 Da, a polydispersity of 1.0, and a higher weight percent of peak 8 than other LMWHs. In some embodiments, one or more monosaccharide or disaccharide is added or removed, and/or one or more acetyl group and/or sulfo group is substituted, removed or added, to modify the activity of the heparin.

In some embodiments, the composition is administered as a dry formulation. In some embodiments, the dry formulation includes heparin particles having a mean geometric diameter of 1 to 500 microns, e.g., particles having a mean geometric diameter of at least 2, 3, 4, 5, 10, 15, 20, 25, 30, 35, 40, 45, 50 or 100 microns. In other embodiments, the composition is administered as a liquid formulation (e.g., an aerosol, mist, or a suspension).

In some embodiments, the composition further includes one or more delivery enhancers, e.g., one or more of a surfactant, an absorption enhancer, protease inhibitor, etc.

In some embodiments, the composition is administered from a device for pulmonary delivery, e.g., a pressurized or non-pressurized container or dispenser, e.g., a pressurized contained or dispenser which contains a suitable propellant and/or nebulizer, or is user activated. In one embodiment, the composition is administered from a delivery device for pulmonary delivery that delivers a metered dose of the composition to a subject.

In some embodiments, at least a portion of the therapeutic or prophylactic agent is delivered to the upper lung, e.g., at least 5%, 10%, 20%, 30%, 40%, 50%, 60%, 70%, 80%, 90% or more of the therapeutic or prophylactic agent is delivered to the upper lung.

In some embodiments, the bioavailability of the therapeutic or prophylactic agent is at least 5%, 10%, 20%, 30%, 40%, 50%, 60%, 70%, 80%, 90% greater than the bioavailability of the therapeutic or prophylactic agent in the absence of the heparin.

In another aspect, the invention features a method of delivering therapeutically effective amounts of insulin to a subject. The method includes: administering to the pulmonary tissue of a subject a composition that includes an effective amount of insulin and a polysaccharide, e.g., as described herein, to thereby deliver the insulin to the subject.

In a preferred embodiment the polysaccharide is a LMWH and is chosen from the group of: enoxaparin, dalteparin, reviparin, tinzaparin, nadroparin, certoparin, ardeparin, and pamaparin.

In some embodiments, the heparin is modified from unfractionated or fractionated heparin (LMWH). In some embodiments, the heparin is modified from a fractionated heparin selected from the group consisting of: enoxaparin, dalteparin, reviparin, tinzaparin, nadroparin, certoparin, ardeparin, and pamaparin.

In one embodiment, the heparin consists of about two, three, four, five, six, seven, eight, nine, ten, eleven, twelve, thirteen, fourteen, fifteen, sixteen, seventeen, eighteen, nineteen or twenty disaccharides. It is particularly preferred that the polysaccharide is a hexasaccharide or larger, and even more preferrably, an octasaccharide or larger.

In one embodiment, the heparin is modified such that the size of the heparin is reduced as compared to a reference standard, e.g., a commercially available version of the heparin or a heparin from which the modified heparin is derived. The size of the heparin can be reduced, e.g., by at least 5%, 10%, 15%, 20%, 30%, 40%, 50%, 60%, 70% or more as compared to the reference standard. In one embodiment, the size of the provided heparin can be reduced, e.g., by a method described herein.

In another embodiment, the heparin is modified such that the charge of the heparin is modified, e.g., increased or decreased, as compared to a reference standard, e.g., a commercially available version of the heparin or a heparin from which the modified heparin is derived. Decreasing the charge of a heparin is also referred to herein as "neutralizing" the charge. In some embodiments, when the charge of the heparin is neutralized, the net negative or net positive charge of the heparin can be reduced by at least 10%, 20%, 30%, 40%, 50%, 60%, 70%, 80%, or 90%. In other embodiments, when the charge of the heparin is neutralized, it can be neutralized such that there is a net negative and net positive charge of 0. The heparin can be neutralized, e.g., by a method described herein. In other embodiments, the net charge of the polysaccharide is increased, e.g., by a method described herein.

In a preferred embodiment the polysaccharide is modified such that it has an anti-Xa activity and/or anti-IIa activity that is reduced by at least 30%, 40%, 50%, 60%, 70%, 80%, 90%, 95%, 99% or more as compared to a reference standard, to thereby deliver the therapeutic or prophylactic agent to the subject. In one embodiment, the reference standard is the level of anti-Xa activity and/or anti-IIa activity of a commercially available version of the heparin or is the level of anti-Xa activity and/or anti-IIa activity of the heparin prior modification. In other embodiments, a heparin is selected based upon similarities between its chemical signature and the chemical signature of one or more polysaccharides involved in lung activity, e.g., normal physiology and/or homeostasis.

In some embodiments, the insulin can be one or more of: insulin lispro, insulin (bovine), insulin, insulin aspart, and insulin analogue.

In some embodiments, the insulin is admixed with the heparin. Admixtures can be prepared, e.g., by mixing, covalently-linked polysaccharides, ionically-linked polysaccharides, spraying drying and other techniques known in the art. In other embodiments, the insulin is linked to one or more heparin in the formulation. As an example, insulin may be linked to a heparin for delivery via known chemistries such as EDC, $CNBH_4$/DMSO/Acetic Acid, etc.

In some embodiments, the heparin is one in which one or more chemical signatures of a oligosaccharide of the heparin that include the structure: $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$, is modified to reduce the anti-Xa activity of the heparin. In some embodiments, the heparin includes the structure of at least one of $\Delta UH_{NAc,6S}GH_{NS,3S,6S}$ or $\Delta UH_{NAc,6S}GH_{NS,3S}$. In some embodiments, the heparin is M118, which has a molecular weight of 5,000 Da, a polydispersity of 1.0, and a higher weight percent of peak 8 than other LMWHs. In some embodiments, one or more monosaccharide or disaccharide is added or removed, and/or one or more acetyl group and/or sulfo group is substituted, removed or added, to modify the activity of the heparin.

In some embodiments, the composition is administered as a dry formulation. In some embodiments, the dry formulation includes heparin particles having a mean geometric diameter of 1 to 500 microns, e.g., particles having a mean geometric diameter of at least 2, 3, 4, 5, 10, 15, 20, 25, 30, 35, 40, 45, 50 or 100 microns. In other embodiments, the composition is administered as a liquid formulation (e.g., an aerosol, mist, or a suspension).

In some embodiments, the composition further includes one or more delivery enhancers, e.g., one or more of a surfactant, an absorption enhancer, protease inhibitor, etc.

In some embodiments, the composition is administered from a device for pulmonary delivery, e.g., a pressurized or non-pressurized container or dispenser, e.g., a pressurized contained or dispenser which contains a suitable propellant and/or nebulizer, or is user activated. In one embodiment, the composition is administered from a delivery device for pulmonary delivery that delivers a metered dose of the composition to a subject.

In some embodiments, at least a portion of the insulin is delivered to the upper lung, e.g., at least 5%, 10%, 20%, 30%, 40%, 50%, 60%, 70%, 80%, 90% or more of the insulin is delivered to the upper lung.

In some embodiments, the bioavailability of the insulin is at least 5%, 10%, 20%, 30%, 40%, 50%, 60%, 70%, 80%, 90% or more greater than the bioavailability of the insulin delivered by pulmonary routes in the absence of the heparin.

In one embodiment, the subject has diabetes, and the insulin in the composition is administered in a dose of about 0.5 to 300 units/kg/day, preferably 1 to 250 units/kg/day, 5 to 200 units/kg/day, 10 to 150 units/kg/day, 25 to 100 units/kg/day and integers in-between. The composition can be administered, e.g., one, two, three, four, five, six or more times a day. In one embodiment, the composition is administered in response to one or more of: a meal and a blood glucose assay.

In one embodiment, the composition is delivered such that peak insulin levels are reached within 5 minutes up to 5 hours after delivery. For example, peak insulin levels can be reached within 10 minutes up to 4 hours, within 30 minutes to 3 hours, or within 1 to 2 hours. In one embodiment, peak insulin levels are reached within 1 hour after delivery. Insulin levels can be measured, e.g., by monitoring insulin levels in the blood and/or blood glucose levels.

In one embodiment, the composition is delivered in a metered dose, e.g., a dose of at least 0.5 IU/kg, 1 IU/kg, 5

IU/kg, 10 IU/kg, 15 IU/kg, 20 IU/kg, 25 IU/kg, 50 IU/kg, 100 IU/kg, 150 IU/kg, 200 IU/kg, 220 IU/kg, 250 IU/kg, and integers in between, and the bioavailability of the insulin is at least about 10, 100, 1000, 10000, 100000 μIU/ml in about 5 minutes to 5 hours, 10 minutes to 4 hours, 30 minutes to 3 hours or 1 to 2 hours after delivery.

In another aspect, the invention features a method of delivering therapeutically effective amounts of human growth hormone to a subject. The method includes: administering to the pulmonary tissue of a subject a composition that includes an effective amount of human growth hormone and a polysaccharide, e.g., such as described herein, to thereby deliver the human growth hormone to the subject.

In a preferred embodiment the polysaccharide is a LMWH and is chosen from the group of: enoxaparin, dalteparin, reviparin, tinzaparin, nadroparin, certoparin, ardeparin, and parnaparin.

In one embodiment, the subject has one or more of the following disorders: growth hormone deficiency (GHD), cardiovascular risk associated with GHD, Turner's syndrome, multiple sclerosis, chronic renal insufficiency, Prader-Willi syndrome or growth retardation due to GHD in children. In one embodiment, the reference standard is the level of anti-Xa activity and/or anti-IIa activity of a commercially available version of the heparin or is the level of anti-Xa activity and/or anti-IIa activity of the heparin prior modification. In other embodiments, a heparin is selected based upon similarities between its chemical signature and the chemical signature of one or more polysaccharides involved in lung activity, e.g., normal physiology and/or homeostasis.

In some embodiments, the heparin is modified from unfractionated or fractionated heparin (LMWH). In some embodiments, the heparin is modified from a fractionated heparin selected from the group consisting of: enoxaparin, dalteparin, reviparin, tinzaparin, nadroparin, certoparin, ardeparin, and parnaparin.

In one embodiment, the heparin consists of about two, three, four, five, six, seven, eight, nine, ten, eleven, twelve, thirteen, fourteen, fifteen, sixteen, seventeen, eighteen, nineteen or twenty disaccharides. It is particularly preferred that the polysaccharide is a hexasaccharide or larger, and even more preferrably, an octasaccharide or larger.

In one embodiment, the heparin is modified such that the size of the heparin is reduced as compared to a reference standard, e.g., a commercially available version of the heparin or a heparin from which the modified heparin is derived. The size of the heparin can be reduced, e.g., by at least 5%, 10%, 15%, 20%, 30%, 40%, 50%, 60%, 70% or more as compared to the reference standard. In one embodiment, the size of the provided heparin can be reduced, e.g., by a method described herein.

In another embodiment, the heparin is modified such that the charge of the heparin is modified, e.g., increased or decreased, as compared to a reference standard, e.g., a commercially available version of the heparin or a heparin from which the modified heparin is derived. Decreasing the charge of a heparin is also referred to herein as "neutralizing" the charge. In some embodiments, when the charge of the heparin is neutralized, the net negative or net positive charge of the heparin can be reduced by at least 10%, 20%, 30%, 40%, 50%, 60%, 70%, 80%, or 90%. In other embodiments, when the charge of the heparin is neutralized, it can be neutralized such that there is a net negative and net positive charge of 0. The heparin can be neutralized, e.g., by a method described herein. In other embodiments, the net charge of the polysaccharide is increased, e.g., by a method described herein.

In a preferred embodiment the polysaccharide is modified such that it has an anti-Xa activity and/or anti-IIa activity that is reduced by at least 30%, 40%, 50%, 60%, 70%, 80%, 90%, 95%, 99% or more as compared to a reference standard, to thereby deliver the therapeutic or prophylactic agent to the subject. In one embodiment, the reference standard is the level of anti-Xa activity and/or anti-IIa activity of a commercially available version of the heparin or is the level of anti-Xa activity and/or anti-IIa activity of the heparin prior modification. In other embodiments, a heparin is selected based upon similarities between its chemical signature and the chemical signature of one or more polysaccharides involved in lung activity, e.g., normal physiology and/or homeostasis.

In some embodiments, the human growth hormone is admixed with the heparin. Admixtures can be prepared, e.g., by mixing, covalently-linked polysaccharides, ionically-linked polysaccharides, spraying drying and other techniques known in the art. In other embodiments, the human growth hormone is linked to one or more heparin in the formulation. As an example, human growth hormone may be linked to a heparin for delivery via known chemistries such as EDC, $CNBH_4$/DMSO/Acetic Acid, etc.

In some embodiments, the heparin is one in which one or more chemical signatures of a oligosaccharide of the heparin that include the structure: $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$, is modified to reduce the anti-Xa activity of the heparin. In some embodiments, the heparin includes the structure of at least one of $\Delta UH_{NAc,6S}GH_{NS,3S,6S}$ or $\Delta UH_{NAc,6S}GH_{NS,3S}$. In some embodiments, the heparin is M118, which has a molecular weight of 5,000 Da, a polydispersity of 1.0, and a higher weight percent of peak 8 than other LMWHs. In some embodiments, one or more monosaccharide or disaccharide is added or removed, and/or one or more acetyl group and/or sulfo group is substituted, removed or added, to modify the activity of the heparin.

In some embodiments, the composition is administered as a dry formulation. In some embodiments, the dry formulation includes heparin particles having a mean geometric diameter of 1 to 500 microns, e.g., particles having a mean geometric diameter of at least 2, 3, 4, 5, 10, 15, 20, 25, 30, 35, 40, 45, 50 or 100 microns. In other embodiments, the composition is administered as a liquid formulation (e.g., an aerosol, mist, or a suspension).

In some embodiments, the composition further includes one or more delivery enhancers, e.g., one or more of a surfactant, an absorption enhancer, protease inhibitor, etc.

In some embodiments, the composition is administered from a device for pulmonary delivery, e.g., a pressurized or non-pressurized container or dispenser, e.g., a pressurized contained or dispenser which contains a suitable propellant and/or nebulizer, or is user activated. In one embodiment, the composition is administered from a delivery device for pulmonary delivery that delivers a metered dose of the composition to a subject.

In some embodiments, at least a portion of the human growth hormone is delivered to the upper lung, e.g., at least 5%, 10%, 20%, 30%, 40%, 50%, 60%, 70%, 80%, 90% or more of the human growth hormone is delivered to the upper lung.

In some embodiments, the bioavailability of the human growth hormone is at least 5%, 10%, 20%, 30%, 40%, 50%, 60%, 70%, 80%, 90% or more greater than the bioavailability of the human growth hormone delivered by pulmonary routes in the absence of the heparin.

In one embodiment, the composition is administered in a dose such that about 0.01 mg to 15 mg are delivered per day, preferably 0.05 to 10 mg/day, 0.1 to 5 mg/day, 0.5 to 2 mg/day, and integers in-between. The composition can be administered, e.g., one, two, three, four or more times a day. In one embodiment, the subject is an adult with GHD and the composition is administered in a dose such that about 0.01 mg to 15 mg are delivered per day, preferably 0.05 to 10 mg/day, 0.1 to 5 mg/day, 0.5 to 2 mg/day, and integers in-between. In one embodiment, the subject is a child with, e.g., GHD, and the human growth hormone in the composition is administered in a dose such that about 0.01 to about 1 mg, 0.05 to about 0.5 mg, and integers in-between, of human growth hormone is delivered per day. In another embodiment, the subject has Turner's syndrome, and the human growth hormone in the composition is administered in a dose such that about 0.01 mg/kg/day, 0.05 mg/kg/day, 0.1 mg/kg/day, 0.5 mg/kg/day, 1 mg/kg/day or 2 mg/kg/day are delivered to the subject. In yet another embodiment, the subject has one or more of chronic renal insufficiency, SGA or intrauterine growth retardation and Prader-Willi syndrome and the human growth hormone in the composition is administered in a dose such that about 0.05 mg/kg/day, 0.1 mg/kg/day, 0.5 mg/kg/day, 1 mg/kg/day, 1.5 mg/kg/day or 2 mg/kg/day are delivered to the subject.

In one embodiment, the composition is delivered such that peak human growth hormone levels are reached within 5 minutes up to 5 hours after delivery. For example, peak human growth hormone levels can be reached within 10 minutes up to 4 hours, within 30 minutes to 3 hours, or within 1 to 2 hours. In one embodiment, peak human growth hormone levels are reached within 1 hour after delivery. Human growth hormone levels can be measured, e.g., by monitoring human growth hormone levels in the blood. In some embodiments, human growth hormone activity can be measured by, e.g., serum IGF-I levels and/or changes in body composition.

In one embodiment, the composition is delivered in a metered dose, e.g., a dose of at least 0.5 IU/kg, 1 IU/kg, 5 IU/kg, 10 IU/kg, 15 IU/kg, 20 IU/kg, 25 IU/kg, 50 IU/kg, 100 IU/kg, 150 IU/kg, 200 IU/kg, 220 IU/kg, 250 IU/kg, and integers in between, and the bioavailability of the human growth hormone is at least about 5 ng/ml, 10 ng/ml, 15 ng/ml, 20 ng/ml, 25 ng/ml, 30 ng/ml, 40 ng/ml, 50 ng/ml or greater in about 5 minutes to hours, 10 minutes to 4 hours, 30 minutes to 3 hours or 1 to 2 hours after delivery.

In another aspect, the invention features a method of delivering therapeutically effective amounts of an interferon, e.g., interferon α and/or interferon β, to a subject. The method includes: administering to the pulmonary tissue of a subject a composition that includes an effective amount of an interferon and a polysaccharide, e.g., such as described herein, to thereby deliver the interferon to the subject.

In a preferred embodiment the polysaccharide is a LMWH and is chosen from the group of: enoxaparin, dalteparin, reviparin, tinzaparin, nadroparin, certoparin, ardeparin, and parnaparin.

In one embodiment, the subject has one or more of: a cancer (e.g., cancer of the kidney, melanoma, multiple myeloma, carcinoid tumors, lymphoma and leukemia), hepatitis (e.g., hepatitis B and hepatitis C), and multiple sclerosis. In one embodiment, the reference standard is the level of anti-Xa activity and/or anti-IIa activity of a commercially available version of the heparin or is the level of anti-Xa activity and/or anti-IIa activity of the heparin prior modification. In other embodiments, a heparin is selected based upon similarities between its chemical signature and the chemical signature of one or more polysaccharides involved in lung activity, e.g., normal physiology and/or homeostasis.

In some embodiments, the heparin is modified from unfractionated or fractionated heparin (LMWH). In some embodiments, the heparin is modified from a fractionated heparin selected from the group consisting of: enoxaparin, dalteparin, reviparin, tinzaparin, nadroparin, certoparin, ardeparin, and pamaparin.

In one embodiment, the heparin consists of about two, three, four, five, six, seven, eight, nine, ten, eleven, twelve, thirteen, fourteen, fifteen, sixteen, seventeen, eighteen, nineteen or twenty disaccharides. It is particularly preferred that the polysaccharide is a hexasaccharide or larger, and even more preferrably, an octasaccharide or larger.

In one embodiment, the heparin is modified such that the size of the heparin is reduced as compared to a reference standard, e.g., a commercially available version of the heparin or a heparin from which the modified heparin is derived. The size of the heparin can be reduced, e.g., by at least 5%, 10%, 15%, 20%, 30%, 40%, 50%, 60%, 70% or more as compared to the reference standard. In one embodiment, the size of the provided heparin can be reduced, e.g., by a method described herein.

In another embodiment, the heparin is modified such that the charge of the heparin is modified, e.g., increased or decreased, as compared to a reference standard, e.g., a commercially available version of the heparin or a heparin from which the modified heparin is derived. Decreasing the charge of a heparin is also referred to herein as "neutralizing" the charge. In some embodiments, when the charge of the heparin is neutralized, the net negative or net positive charge of the heparin can be reduced by at least 10%, 20%, 30%, 40%, 50%, 60%, 70%, 80%, or 90%. In other embodiments, when the charge of the heparin is neutralized, it can be neutralized such that there is a net negative and net positive charge of 0. The heparin can be neutralized, e.g., by a method described herein. In other embodiments, the net charge of the polysaccharide is increased, e.g., by a method described herein.

In a preferred embodiment the polysaccharide is modified such that it has an anti-Xa activity and/or anti-IIa activity that is reduced by at least 30%, 40%, 50%, 60%, 70%, 80%, 90%, 95%, 99% or more as compared to a reference standard, to thereby deliver the therapeutic or prophylactic agent to the subject. In one embodiment, the reference standard is the level of anti-Xa activity and/or anti-IIa activity of a commercially available version of the heparin or is the level of anti-Xa activity and/or anti-IIa activity of the heparin prior modification. In other embodiments, a heparin is selected based upon similarities between its chemical signature and the chemical signature of one or more polysaccharides involved in lung activity, e.g., normal physiology and/or homeostasis.

In some embodiments, the insulin can be one or more of: insulin lispro, insulin (bovine), insulin, insulin aspart, and insulin analogue.

In some embodiments, the interferon is admixed with the heparin. Admixtures can be prepared, e.g., by mixing, covalently-linked polysaccharides, ionically-linked polysaccharides, spraying drying and other techniques known in the art. In other embodiments, the interferon is linked to one or more heparin in the formulation. As an example, interferon may be linked to a heparin for delivery via known chemistries such as EDC, $CNBH_4$/DMSO/Acetic Acid, etc.

In some embodiments, the heparin is one in which one or more chemical signatures of a oligosaccharide of the heparin that include the structure: $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$, is modified to reduce the anti-Xa activity of the heparin. In some embodiments, the heparin includes the structure of at least one of $\Delta UH_{NAc,6S}GH_{NS,3S,6S}$ or $\Delta UH_{NAc,6S}GH_{NS,3S}$. In some embodiments, the heparin is M118, which has a molecular weight of 5,000 Da, a polydispersity of 1.0, and a higher weight percent of peak 8 than other LMWHs. In some embodiments, one or more monosaccharide or disaccharide is added or removed, and/or one or more acetyl group and/or sulfo group is substituted, removed or added, to modify the activity of the heparin.

In some embodiments, the composition is administered as a dry formulation. In some embodiments, the dry formulation includes heparin particles having a mean geometric diameter of 1 to 500 microns, e.g., particles having a mean geometric diameter of at least 2, 3, 4, 5, 10, 15, 20, 25, 30, 35, 40, 45, 50 or 100 microns. In other embodiments, the composition is administered as a liquid formulation (e.g., an aerosol, mist, or a suspension).

In some embodiments, the composition further includes one or more delivery enhancers, e.g., one or more of a surfactant, an absorption enhancer, protease inhibitor, etc.

In some embodiments, the composition is administered from a device for pulmonary delivery, e.g., a pressurized or non-pressurized container or dispenser, e.g., a pressurized contained or dispenser which contains a suitable propellant and/or nebulizer, or is user activated. In one embodiment, the composition is administered from a delivery device for pulmonary delivery that delivers a metered dose of the composition to a subject.

In some embodiments, at least a portion of the interferon is delivered to the upper lung, e.g., at least 5%, 10%, 20%, 30%, 40%, 50%, 60%, 70%, 80%, 90% or more of the interferon is delivered to the upper lung.

In some embodiments, the bioavailability of the interferon is at least 5%, 10%, 20%, 30%, 40%, 50%, 60%, 70%, 80%, 90% or more greater than the bioavailability of the interferon delivered by pulmonary routes in the absence of the heparin.

In one embodiment, the composition is delivered such that peak interferon levels are reached within 5 minutes up to 15 hours after delivery. For example, peak interferon levels can be reached within 10 minutes up to 10 hours, within 30 minutes to 7 hours, or within 1 to 5 hours. Interferon levels can be measured, e.g., by monitoring interferon levels in the blood.

In one embodiment, the composition is delivered in a metered dose, e.g., a dose that results in the bioavailability of the interferon being at least about 3 IU/ml, 5 IU/ml, 7 IU/ml, 10 IU/ml, 15 IU/ml or 20 IU/ml in about 10 minutes up to 10 hours, 30 minutes to 7 hours, or 1 to 5 hours after delivery.

DETAILED DESCRIPTION OF THE INVENTION

Figure 1:
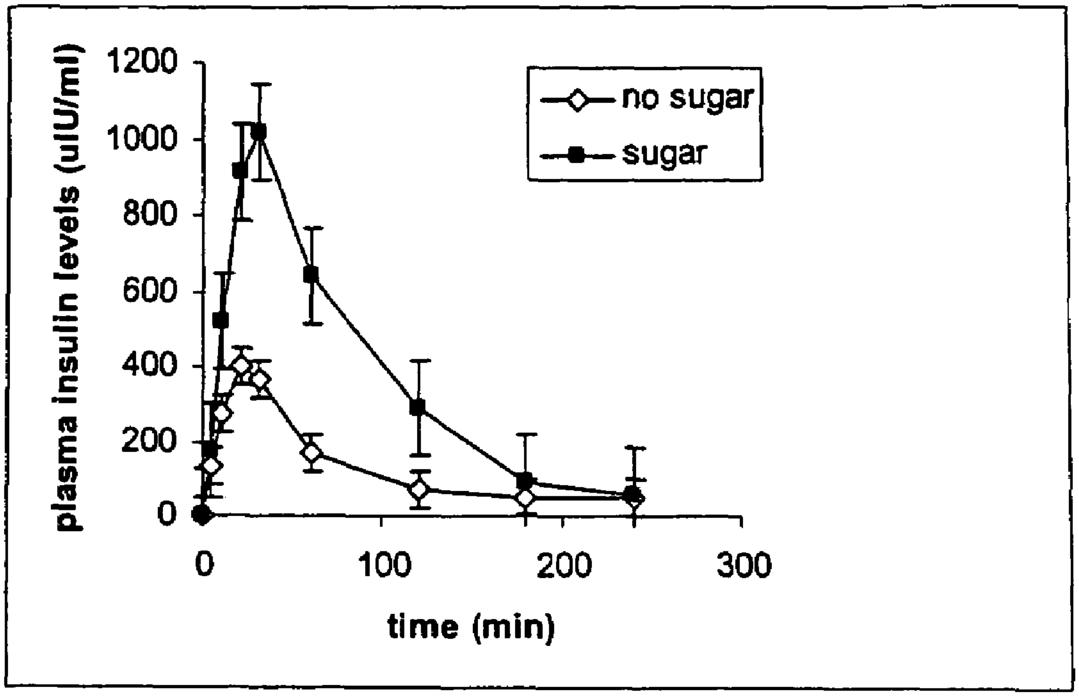
FIG. 1: Polysaccharide-mediated insulin delivery: Insulin was formulated with ardeparin to produce particle size less than 75 μm for administration. Rats (Sprague-Dawley, 250-350 g) were anaesthetized, intubated with a carotid catheter for blood withdrawal, and an insufflator containing the polysaccharide/insulin material was inserted intratracheally for pulmonary delivery. Blood was sampled at various time points, collected in 3.8% sodium citrate, and centrifuged to isolate the plasma. Plasma insulin levels were detected using an ELISA kit.
Figure 2A:
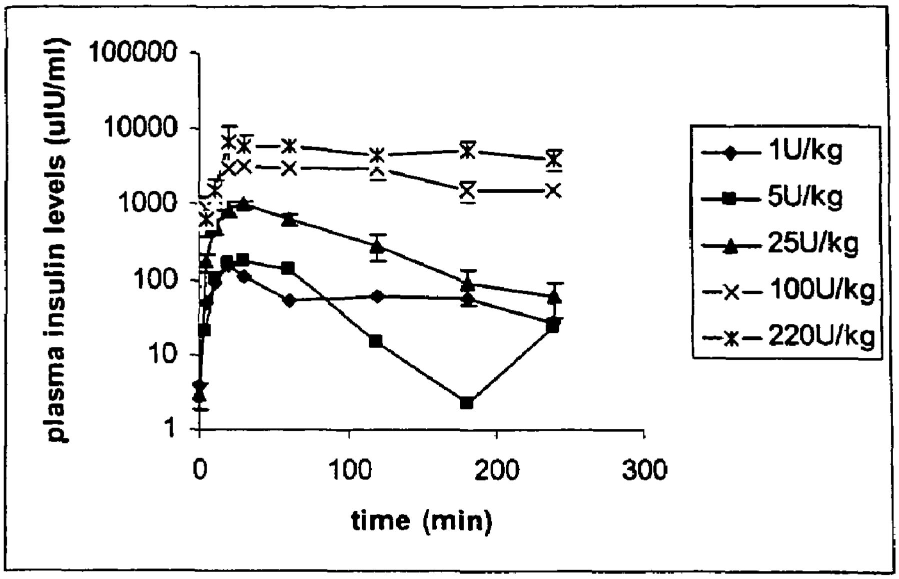
FIG. 2A-C: Insulin Dose response: (A) Rats were treated as described in FIG. 1. The ratio of insulin to ardeparin was altered in each condition by increasing the insulin dose and holding constant the polysaccharide amount. (B) Rats were treated as described in FIG. 1. The ratio of insulin to polysaccharide was altered in each condition by increasing the insulin dose and holding constant the polysaccharide amount. (C) Data from insulin dosing experiments were analyzed by calculating the area under the curve for each condition and are shown graphically as a function of dose.
Figure 2B:
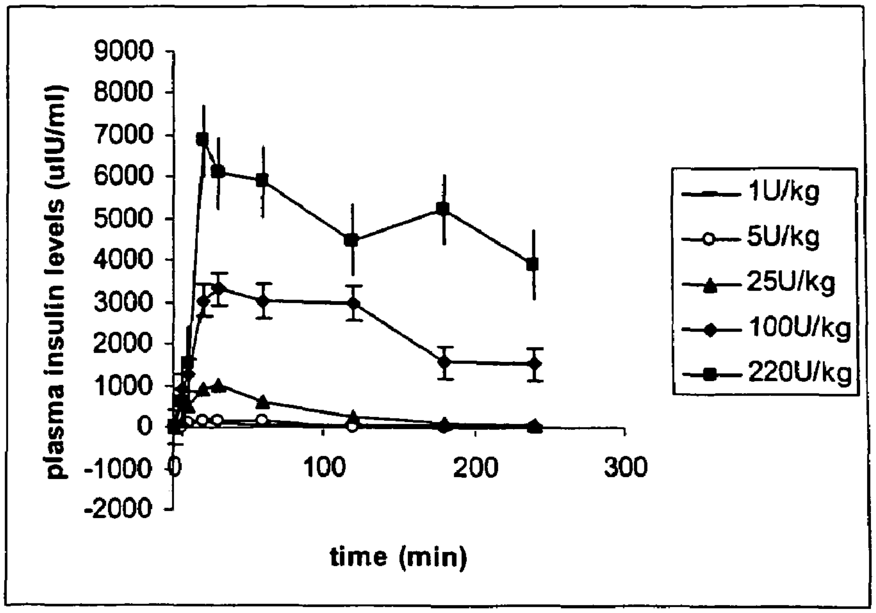
Figure 2C:
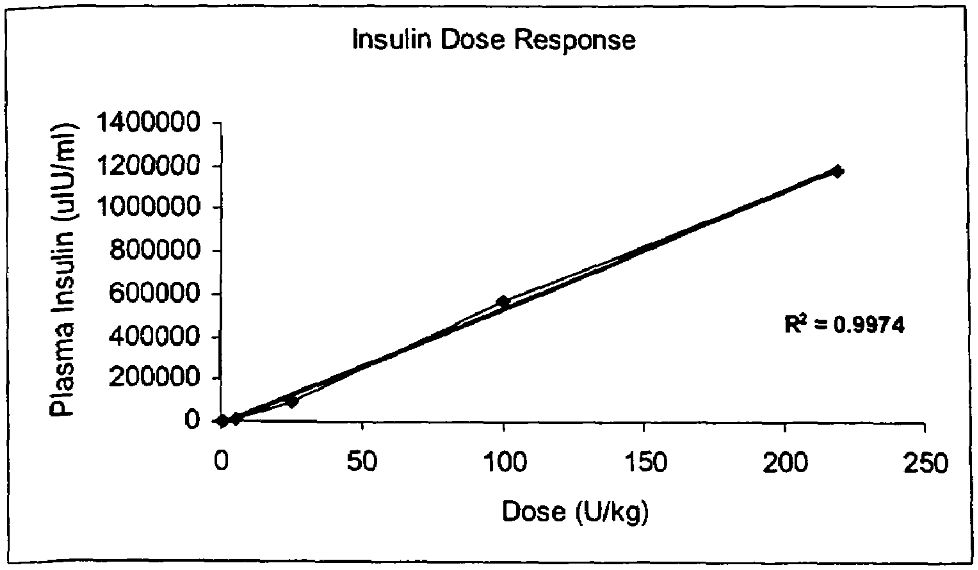
Figure 3:
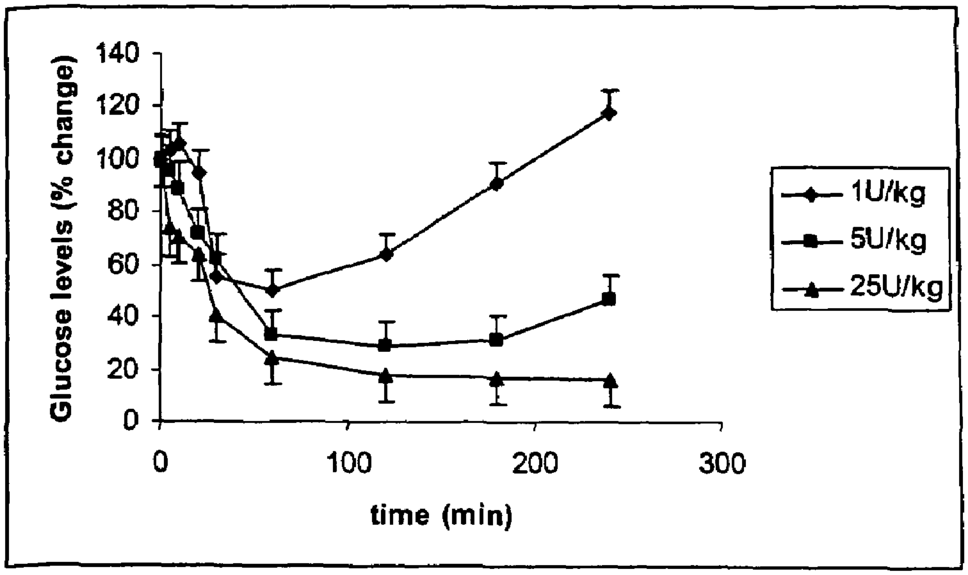
FIG. 3: Pharmacodynamics of pulmonary insulin: Rats were treated as described in FIG. 1. Insulin dosing was altered, as described in FIG. 2, to be in the physiologic range. Blood samples were analyzed at various time points for glucose content using a commercially available blood glucose monitor.
Figure 4:
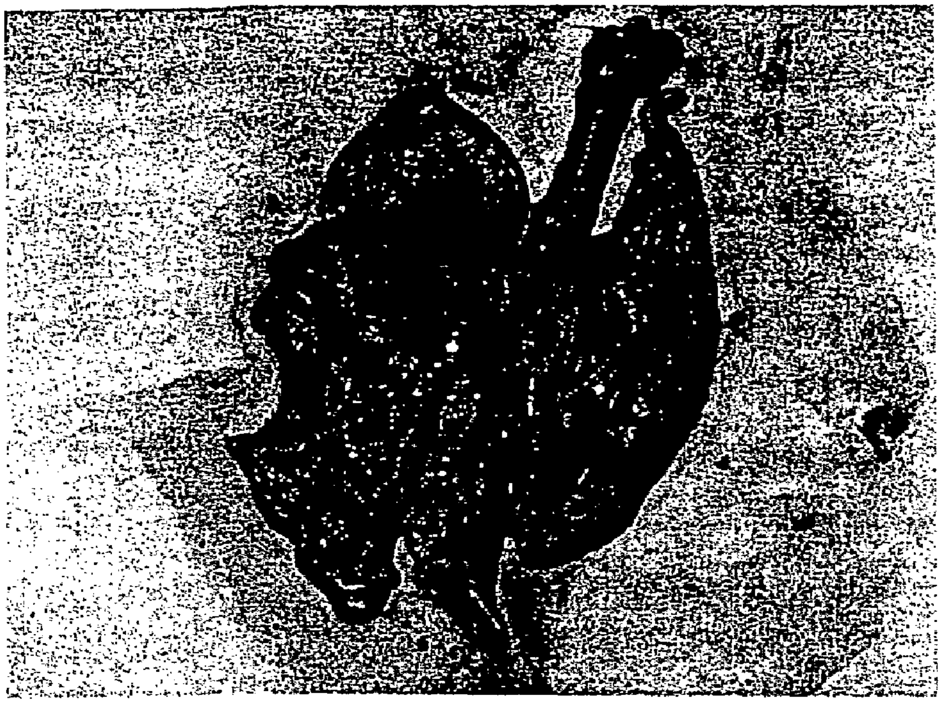
FIG. 4: Upper airway delivery: Ardeparin was formulated with crystal violet dye to produce particle size less than 75 μm for administration. Rats were treated as described in FIG. 1, with the exception that the carotid was not catheterized, and the dye/polysaccharide material was administered intratracheally. Animals were sacrificed immediately, the lungs were excised and dissected, and drug placement was visualized.
Figure 5A:
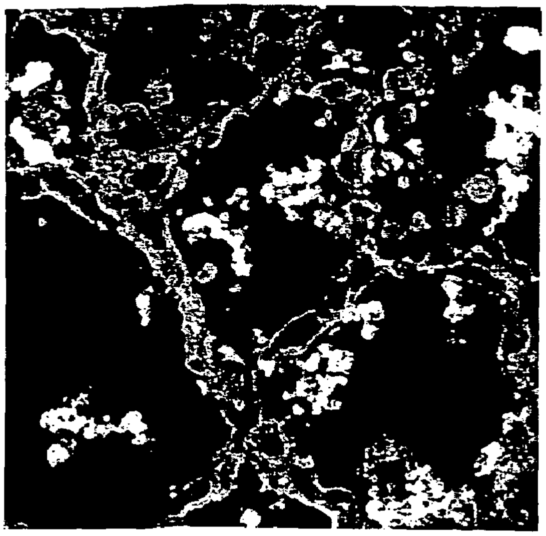
FIGS. 5A&B: Upper airway delivery: Ardeparin was formulated with FITC-insulin to produce particle size less than 75 μm for administration. Rats were treated as described in FIG. 1, with the exception that the carotid was not catheterized, and the drug/polysaccharide material was administered intratracheally. Animals were sacrificed after 10 min, the lungs were perfused with zinc-formalin, and paraffin-processed. Using a confocal microscope, FITC-insulin was visualized in the upper airways (A) and in the deep lung (B).
Figure 5B:
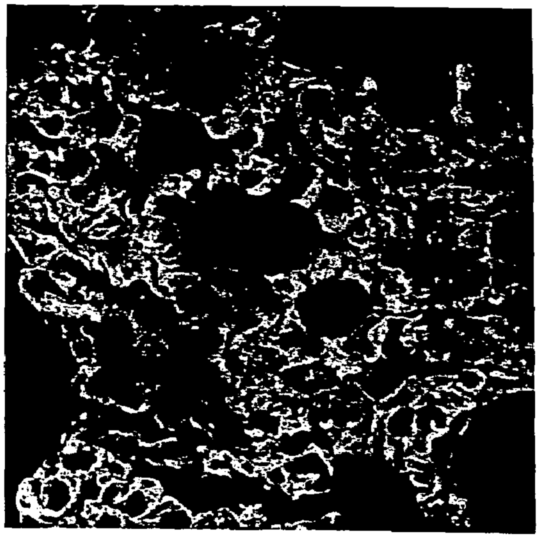
Figure 6:
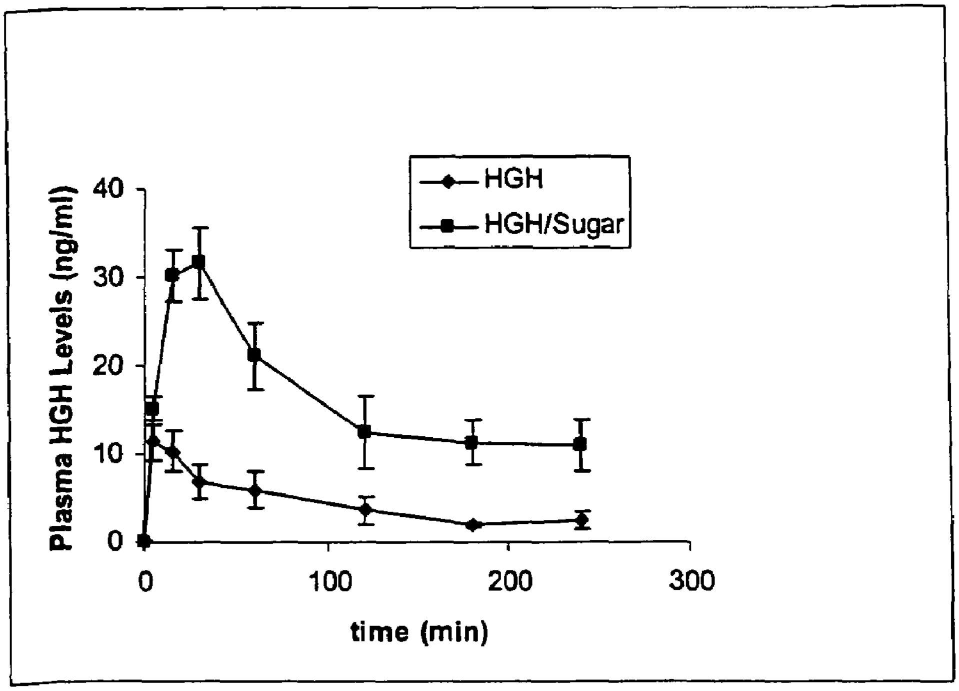
FIG. 6: Polysaccharide-mediated human growth hormone delivery: Ardeparin was formulated with hGH and delivered intratracheally to rats and plasma samples were analyzed for hGH levels. Experiments were performed as described in FIG. 1.

It was discovered that polysaccharides such as heparin and low molecular weight heparin (LMWH) deliver biological agents, regardless of the size of the biological agent, to the systemic circulation via the pulmonary tissue at therapeutically and prophylactically effective levels. In addition, it was found that by reducing the activity of the polysaccharide, e.g., by identifying chemical properties of polysaccharides, the polysaccharides provide enhanced formulations of active agents for pulmonary delivery with reduced side-effects from the polysaccharide.

The methods described herein can be used to deliver biological agents at high levels of bioavailability by an administrative route that in the past had met with limited success. As shown in the Figures, compositions that include a LMWH and a biologically agent, namely insulin or human growth hormone, have been generated which have enhanced pulmonary delivery profiles.

A "polysaccharide" as used herein is a polymer composed of monosaccharides linked to one another. In many polysaccharides, the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide). Polysaccharides include but are not limited to heparin-like glycosaminoglycans and derivatives and analogs thereof, chondroitin sulfate and derivatives and analogs thereof, hyaluronic acid and derivatives or analogs thereof, dermatan sulfate and derivatives or analogs thereof, keratan sulfate and derivatives or analogs thereof, chitin derivatives and analogs thereof, e.g., 6-0-sulfated carboxymethyl chitin, chitosan and derivatives or analogs thereof, immunogenic polysaccharides isolated from *phellinus linteus*, PI-88 (a mixture of highly sulfated oligosaccharide derived from the sulfation of phosphomannum which is purified from the high molecular weight core produced by fermentation of the yeast *pichia holstii*) and its derivatives and analogs, polysaccharide antigens for vaccines, and calcium spirulan (Ca-SP, isolated from blue-green algae, *spirulina platensis*) and derivatives and analogs thereof.

One preferred type of polysaccharide is an HLGAG. Thus, in some embodiments, the polysaccharide is a heparin-like glycosaminoglycan (HLGAG) that has a reduced activity. The methods taught herein are sometimes described with reference to HLGAGs but the properties taught herein can be extended to other polysaccharides, and unless a claim specifies otherwise the claims encompass any polysaccharide. As used herein the terms "HLGAG" and "glycosaminoglycans" are used interchangeably to refer to a family of molecules having heparin like structures and properties. These molecules include but are not limited to low molecular weight heparin (LMWH), heparin, biotechnologically prepared heparin, chemically modified heparin, synthetic heparins, heparin mimetics and heparan sulfate. The term "biotechnological heparin" encompasses heparin that is prepared from natural sources of polysaccharides which have been chemically modified and is described in Razi et al., Bioche. J. 1995 Jul. 15; 309 (Pt 2): 465-72. Chemically modified heparin is described in Yates et al., Carbohydrate Res (1996) November 20; 294:15-27, and is known to those of skill in the art. Synthetic heparin is well known to those of skill in the art. Heparan Sulfate refers to a glycosaminoglycan containing a disaccharide repeat unit similar to heparin, but which has more N-acetyl groups and fewer N- and O-sulfate groups. Heparin mimetics are monosaccharides (e.g., sucralfate), oligosaccharides, or polysaccharides having at least one biological activity of heparin (i.e., anticoagulation, inhibition of cancer, treatment of lung disorders, etc.) or structurally similar properties of heparin. Preferably these molecules are highly sulfated. Heparin mimetics may be naturally occurring, synthetic or chemically modified. (Barchi, J. J., Curr. Pharm. Des., 2000, Mar, 6(4):485-501). The term "HLGAG" also encompasses functional variants of the above-described HLGAG molecules. These functional variants have a similar structure but include slight modifications to the structure.

"LMWH" as used herein refers to a preparation of sulfated glycosaminoglycans (GAGs) having an average molecular weight of less than 8000 Da, with about at least 60% of the oligosaccharide chains of a LMWH preparation having a molecular weight of less than 8000 Da. Several LMWH preparations are commercially available, but, LMWHs can also be prepared from heparin, using e.g., HLGAG degrading enzymes. HLGAG degrading enzymes include but are not limited to heparinase-I, heparinase-II, heparinase-III, heparinase IV, heparanase, D-glucuronidase and L-iduronidase. The three heparinases from *Flavobacterium heparinum* are enzymatic tools that have been used for the generation of LMWH (5,000-8,000 Da) and ultra-low molecular weight heparin (~3,000 Da). Commercially available LMWH include, but are not limited to, enoxaparin (brand name Lovenox, Aventis Pharmaceuticals; other enoxaparins include those made by Opocrin, Gland, Enorin), dalteparin (Fragmin, Pharmacia and Upjohn), certoparin (Sandobarin, Novartis), ardeparin (Normiflo, Wyeth Lederle), nadroparin (Fraxiparine, Sanofi-Winthrop), pamaparin (Fluxum, Wassermann), reviparin (Clivarin, Knoll AG), and tinzaparin (Innohep, Leo Laboratories, Logiparin, Novo Nordisk). Some preferred forms of LMWH include enoxaparin (Lovenox) and dalteparin (Fragmin). A "synthetic heparin" or "synthetic HLGAG" as used herein refers to HLGAGs that are synthesized compounds and are not derived by fragmentation of heparin. Methods of preparing synthetic heparins are provided, for example, in Petitou et al. (1999) *Nature* 398: 417, the contents of which is incorporated herein by reference. The term synthetic heparins also include derivatives thereof.

Methods of Reducing a Biological Activity of a Polysaccharide

The polysaccharides of the invention can be modified to reduce one or more therapeutic activity of the polysaccharide. For example, a heparin can be modified such that one or more activity against Factor Xa and Factor Ia in blood coagulation is reduced.

Polysaccharides can be modified to reduce the therapeutic actions of the polysaccharide, e.g., by reducing the net charge, mass and/or size of the polysaccharide. These modifications can be made either enzymatically or chemically, e.g., as described herein. The resulting activity can then be determined using standard chromogenic assays.

For Xa of a heparin, the activity can be based on a sequence of a oligosaccharide comprising peak 8 or a tetrasaccharide within that structure. There are several ways to reduce anti-Xa activity of a heparin. For example, one or more of the following can be done to a heparin that includes the structures $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$: lower the sulfation, modify the functional groups with non-sulfates, and reduce the size of the chain to below the oligosaccharide. Specifically, removal of 2-O, 3-O, 6-O, and/or N-sulfates, in various combinations, can be used to completely, or in partially, reduce the anti-Xa activity of a heparin.

For IIa of a heparin, that activity can be based on an octadecasaccharide (18-) that also contains the peak 8. Thus, the same approaches can be used as for reducing anti-IIa activity as is described for reducing anti-Xa activity. The approaches include decreasing the molecular weight/size of the chain.

Methods that can be used to modulate the activity of a polysaccharide and methods that can be used to test the activity of the modified polysaccharide are described below.

Methods of Determining the Chemical Signature of a Polysaccharide and Methods of Modulating Activity, Charge and/or Size of a Polysaccharide In addition to modifying the polysaccharide to reduce a therapeutic activity of the polysaccharide, the polysaccharide can also be modified to alter the net charge, mass and/or size of the polysaccharide. The pulmonary delivery profiles, described herein, can be further enhanced, e.g., by neutralizing a polysaccharide, adding charged elements to a polysaccharide, and/or reducing the mass of the polysaccharide, and/or the mass of the structure. For example, using the chemical signature of the polysaccharide, charges can be modulated, e.g., neutralized or enhanced, and/or the size of the polysaccharide reduced.

A "neutralized formulation" as used herein is a formulation in which the net negative or positive charge has been reduced or masked by at least 10%. In other embodiments, the neutralized formulation is a formulation in which the net negative or positive charge has been reduced by at least 20%, 30%, 40%, 50%, 60%, 70%, 80, 90% or 100% or any integer there between. A "completely neutral" formulation is one in which there is a net negative and positive charge of zero.

Specific chemical properties of a polysaccharide may be identified and manipulated in order to reduce a specific therapeutic activity of the polysaccharide and/or enhance delivery of one or more active agent(s) by pulmonary routes. The chemical properties of the polysaccharide may be altered by various techniques in order to reduce the biological activity of the polysaccharide and/or enhance delivery of an active agent (e.g., a therapeutic, prophylactic or diagnostic agent) associated with polysaccharides. Methodologies have been developed to determine chemical signatures of polysaccharides. A chemical signature, as used herein, refers to information regarding, e.g., the identity and number the mono- and disaccharide building blocks of a polysaccharide, information regarding the physiochemical properties such as the overall (also referred to as the "net charge"), charge density, molecular size, charge to mass ratio and the presence of iduronic and/or glucuronic acid content as well as the relationships between the mono- and disaccharide building blocks, and active sites associated with these building blocks. As described herein, it is possible to use specific chemical signatures to formulate polysaccharides with one or more reduced therapeutic activity and/or enhanced pulmonary delivery properties. The chemical signature can be provided by determining one or more primary outputs chosen from the following: the presence or the amount of one or more component saccharides or disaccharides; the presence or the amount of one or more block components, wherein a block component is one made up of more than one saccharides or polysaccharide;

The presence or amount of one or more saccharide-representative, wherein a saccharide-representative is a saccharride modified to enhance detectability; the presence or amount of an indicator of three dimensional structure or a parameter related to three dimensional structure, e.g., activity, e.g., the presence or amount of a structure produced by cross-linking a polysaccharide, e.g., the cross-linking of specific saccharides which are not adjacent in the linear sequence; or the presence or amount of one or more modified saccharides, wherein a modified saccharide is one present in a starting material used to make a preparation but which is altered in the production of the preparation, e.g., a saccharide modified by cleavage. The chemical signature can also be provided by determining a secondary output, which include one or more of: total charge; density of charge.

With regard to heparins, the terms, "1" or "peak 1" refers to $\Delta U_{2S}H_{NS,6S}$; "2" or "peak 2" refers to $\Delta U_{2S}H_{NS}$; "3" or "peak 3" refers to $\Delta UH_{NS,6S}$; "4" or "peak 4" refers to $\Delta U_{2S}H_{NAC,6S}$; "5" or "peak 5" refers to $\Delta UH_{NS}$; "6" or "peak 6" refers to $\Delta U_{2S}H_{NAC}$; "7" or "peak 7" refers to $\Delta UH_{NAC,6S}$; "8" or "peak 8" refers to $\Delta U\ H_{NAc,6S}GH_{NS,3S,6S}$; $\Delta U\ H_{NS,6S}GH_{NS,3S,6S}$; $\Delta U\ H_{NAc,6S}GH_{NS,3S}$; or $\Delta U\ H_{NS,6S}GH_{NS,3S}$, collectively. The nomenclature "ΔU" refers to an unsaturated Uronic acid (Iduronic acid (I) or Glucuronic acid (G) that has a double bond introduced at the 4-5 position as a result of the lyase action of heparinases. Upon the introduction of the double bond the distinction between the stereo isomers I and U disappears, and hence the notation ΔU: Δ to denote double bond, and U to denote that they can be derived from either I or U. Thus, as used herein, "ΔU" represents both I and G, such that $\Delta U_{2S}H_{NS,6S}$ encompasses both $I_{2S}H_{NS,6S}$ and $G_{2S}H_{NS,6S}$; $\Delta U_{2S}H_{NS}$ encompasses both $I_{2S}H_{NS}$ and $G_{2S}H_{NS}$, and so forth. The process of identifying chemical properties or signatures of a polysaccharide and using this information to generate polysaccharides with one or more reduced therapeutic activity and/or enhanced in vivo delivery capabilities is referred to herein as the process of chemical formulation of a polysaccharide. For example, this information can be used to generate information about structures in heparins that play a role in anti-Xa activity, anti-IIa activity, or other activities of heparins and to use this information to reduce one or more of these activities of heparin.

Chemical formulation involves the preparation of a composition using chemical entities to achieve an appropriate balance for delivery of an active agent, e.g., while reducing the therapeutic activities associated with the particular polysaccharide. The chemical formulation is accomplished using techniques to structurally characterize or sequence polysaccharides and then formulating, e.g., modifying one or more monosaccharide and/or modifying a linkage or a substituent of that monosaccharide such as masking charge or adding a charge based on the structure. This is distinct from physical formulation of a polysaccharide, which refers to the processing of a particle by methods known in the art based on the physical attributes of the particle such as particle size, tap density, etc. that are all physical descriptions of particles. The compositions and methods of the invention involve at a minimum chemical formulation of polysaccharides for efficient pulmonary delivery of an active agent with reduced side effects of the polysaccharide. In addition to the chemical formulation, the polysaccharides may be physically formulated to achieve, e.g., a particular particle size, tap density etc. It has been found that such chemical formulations can enhance pulmonary delivery of an active agent without being physically formulated. One specific chemical property that may be analyzed is charge. Neutralization of the charge of a polysaccharide can, e.g., enhance the ability the polysaccharide to permeate lipid membranes, or permeate epithelial barriers. As used herein the terms "neutralization", "neutralize" and "neutralizing" refer a process for generating a polysaccharide in which the net negative or positive charge of the material has been reduced or masked by at least 10% and in some embodiments by at least 20%, 30%, 40%, 50%, 60%, 70%, 80, 90% or 100 or any integer in between. The net or overall charge of a polysaccharide such as heparin can be calculated by dividing the mass of the heparin by the average molecular weight of a disaccharide (500) and multiplying that number by the average charge per disaccharide (e.g., 2.3). The average charge per disaccharide can vary from polysaccharide to polysaccharide. The average charge is the mean charge for the polysaccharides present in a polydisperse composition. The net charge of each polysaccharide in a composition can vary. Methods of determining the charge of polysaccharides including the charge per disaccharide are described, for example, in Venkataraman, G. et al. *Science,* 286, 537-542 (1999). Charge neutralization may be accomplished in a variety of ways. Preferably, the charge of the polysaccharide is determined. Based on that determination, an appropriate strategy for charge neutralization may be selected, e.g., a strategy which maintains or enhances the delivery properties of the polysaccharide. In general, a more highly charged polysaccharide will be more effectively neutralized with the use of a higher concentration of neutralizing agent to mask the charge. For instance, chemical analysis of a heparin oligosaccharide revealed that the molecule contained a total of 17 negative charges, primarily O-sulfates. Charge neutralization and powder formation of the heparin molecule was accomplished by precipitating the polysaccharide using a 200 mM sodium chloride pH 4.5 solution. Similarly, a heterogeneous population of heparin, such as a low molecular weight heparin was chemically analyzed and found to have an average charge distribution of 24-32 negative charges. Charge neutralization and optimal powder formation of this material was accomplished by using a higher concentration of salt, counterions, and/or a different pH to effectively mask charge.

The neutralization may be accomplished using a charge neutralization agent. A "charge neutralization agent" as used herein is a positively or negatively charged compound that is capable of interacting with an oppositely charged molecule and thereby neutralizing the charge. Charge neutralization agents include but are not limited to counter ions such as mono- and divalent ions including, but not limited to, barium, calcium, sodium, potassium, lithium, ammonium, magnesium and zinc as well as transition metals such as iron, nickel, and copper; and other neutralizing compounds such as small organic compounds, spermine, spermidine, low molecular weight protamine, or basic peptides.

If a polysaccharide is negatively charged, a positively charged compound may be used to neutralize the polysaccharide. Likewise, if the polysaccharide is positively charged, then a negatively charged compound may be used. Once the type and quantity of charge in the polysaccharide is determined, e.g., by chemical analysis, then the appropriate amount of neutralizing compound may be selected. The exact amount neutralizing compound will depend on the particular sample, since the type and amount of charge may vary from sample to sample. In general, a low concentration of neutralizing agent will be sufficient to reduce the charge of a polysaccharide having only a few charged moieties and it is desirable to increase the concentration of the neutralizing agent for more highly charged molecules.

Another chemical property of the polysaccharides that may be considered is the quantity of 2-O sulfated iduronic acid moieties present in the polysaccharide. 2-O sulfated iduronic acid moieties chelate metals in a distinctly different matter than other components of a polysaccharide. As such the nature and amount of counter ions useful for neutralization is somewhat determined by the number and localization of 2-O sulfated iduronic acids in the polysaccharide. For instance, a heparin with a high degree of 2-O sulfated iduronic acid (~80%) was efficiently precipitated using calcium or barium salts instead of sodium salts whereas a heparan sulfate with a low degree of 2-O sulfated iduronic acid was not precipitated in an appropriate manner using these same conditions. In general, a higher degree of 2-O sulfated iduronic acids in a polysaccharide is more effectively formulated with a higher concentration of neutralizing agents.

Additionally, the length of the polysaccharide has an impact on its formulation. Based on the length of the polysaccharide, different types and concentrations of organic modifiers such as organic solvents will have different effects on the formulation properties of the polysaccharide. For instance, different sized heparin oligosaccharides were demonstrated to form optimal powders at various concentrations of organic solvent. In general, the longer an oligosaccharide chain, and the higher its number of charges, the less soluble a polysaccharide is in non-aqueous solutions. As such, based on size and charge density as chemical signatures, powders can be formed via the addition of various volume equivalents of organic modifiers. In general, the longer an oligonucleotide within a particular class of polysaccharides (i.e., HLGAGs), a lower concentration of organic modifier will produce enhanced results.

An organic modifier as used herein is an organic solution such as, for instance, an alcohol and a polar organic solvent, such as acetonitrile, acetone, or dimethylsulfoxide and aqueous mixtures thereof.

The activity, size and/or charge of a polysaccharide can be reduced by digesting the polysaccharide with at least one agent. The agent can be selected, e.g., based upon the information obtained regarding the chemical signature of the polysaccharide. For example, enzymes and/or chemicals can be used which selectively cleave the polysaccharide. Thus, polysaccharides can be generated such that, e.g., regions of the polysaccharide which are involved and/or influence a biological activity can be cleaved, and regions of the polysaccharide which are not involved and/or do not influence a biological activity remain intact. As used herein, the term "intact" means uncleaved and complete.

For example, a LMWH can be generated which has a reduction in at least one activity, e.g., anti-Xa activity and/or anti-IIa activity. Examples of activities mediated by heparin include: anti-Xa activity, anti-IIa activity, protamine neutralization, anticoagulation/antithrombosis, cell proliferation, e.g., unwanted cell proliferation, e.g., unwanted malignant or non-malignant cell proliferation; angiogenesis; inflammatory processes; cell migration; cell activation; cell adhesion. Standard methods of measuring such activities are known. For example, anti-Xa activity can be measured by the amidolytic method on a chromogenic substrate described by Teien et al., Thrombo. Res. 10:399-410 (1977), with a standard being the first international standard for LMWH. Known methods for measuring anti-IIa activity are described, for example, by Anderson et al., Thrombo. Res. 15:531-541 (1979), with a standard being the first international standard for LMWH.

HLGAG fragments may be degraded using for example, enzymes such as heparin lyase enzymes (heparinases) or nitrous acid. They may also be modified using different enzymes that transfer sulfate groups to the specific positions or remove the sulfate groups from those positions. The modifying enzymes are exolytic and nonprocessive which means that they just act once on the non-reducing end and will let go of the heparin chain without sequentially modifying the rest of the chain. For each of the modifiable positions in the disaccharide unit there exits a modifying enzyme. An enzyme that adds a sulfate group is called a sulfotransferase and an enzyme that removes a sulfate group is called a sulfatase. The modifying enzymes include 2-O sulfatase/sulfotransferase, 3-O sulfatase/sulfotransferase, 6-O sulfatase/sulfotransferase and N-deacetylase-N-sulfotransferase. The function of these enzymes is evident from their names, for example a 2-O sulfotransferase transfers a sulfate group to the 2-O position of an iduronic acid (2-O sulfated glucuronic acid is a rare occurrence in the HLGAG chains) and a 2-O sulfatase removes the sulfate group from the 2-O position of an iduronic acid.

HLGAG degrading enzymes include but are not limited to heparinase-I, heparinase-II, heparinase-III, heparinase-IV, heparanase, D-glucuronidase and L-iduronidase, modified versions of heparinases, variants and functionally active fragments thereof. The three heparinases from *Flavobacterium heparinum* are enzymatic tools that have been used for the generation of LMWH (5,000-8,000 Da) and ultra-low molecular weight heparin (≦3,000 Da). Heparinase I cleaves highly sulfated regions of HLGAGs at 2-O sulfated uronic acids, whereas heparinase II has a broader substrate specificity and cleaves glycosidic linkages containing both 2-O sulfated and nonsulfated uronic acids (Ernst, S., Langer, R., Cooney, C. L. & Sasisekliaran, R. (1995) Crit Rev Biochem Mol Biol 30, 3 87-444). Heparinase III, as opposed to heparinase I, cleaves primarily undersulfated regions of HLGAGs, viz., glycosidic linkages containing a nonsulfated uronic acid (Emst, S., Langer, R., Cooney, C. L. & Sasiseldiaran, R. (1995) Crit Rev Biochem Mol Biol 30, 387-444). Several patents and patent applications describe useful modifications and variants and fragments of heparinase, including U.S. Pat. No. 6,217,863 and pending application Ser. Nos. 09/384,959 and 09/802,285. Other modifications and variants are also useful.

Glucuronidase and iduronidase, as their name suggests, cleave at the glycosidic linkage after a glucuronic acid and iduronic acid respectively. Nitrous acid clips randomly at glycosidic linkages after a N-sulfated hexosamine and converts the six membered hexosamine ring to a 5-membered anhydromannitol ring.

Chemicals useful for digesting polysaccharides such as HLGAGS include chemicals chosen from group consisting of oxidative depolymerization with $H_2O_2$ or $Cu^+$ and $H_2O_2$, deaminative cleavage with isoamyl nitrite, or nitrous acid, β-eliminative cleavage with benzyl ester of heparin by alkaline treatment or by heparinase.

Methods for identifying the charge and other properties of polysaccharides have been described in Venkataraman, G., et al., *Science,* 286, 537-542 (1999), and U.S. patent application Ser. Nos. 09/557,997 and 09/558,137, both filed on Apr. 24, 2000, which are hereby incorporated by reference.

Formulated Polysaccharide Compositions

It was found that the polysaccharides of the invention can be used to deliver an active agent without additional agents that enhance delivery or slow release and still result in therapeutically effective levels of the active agent being delivered by pulmonary route.

The compositions can also be generated to be in solid or liquid form. An example of a solid form is dry particles, e.g., dry particles for pulmonary delivery such as those described in PCT Publication Number 02/32406, the contents of which are incorporated herein by reference.

The polysaccharides of the invention may optionally be formulated in a pharmaceutically acceptable carrier. Such preparations may routinely contain pharmaceutically acceptable concentrations of salt, buffering agents, preservatives, compatible carriers, adjuvants, and optionally other therapeutic ingredients. The compositions may further be formulated into specific delivery devices. As described below, the polysaccharide may also be formulated based upon their intended route of delivery.

The compositions of the invention may be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, oxalic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2 mole % W/V); citric acid and a salt (1-3 mole % W/V); boric acid and a salt (0.5-2.5 mole % W/V); and phosphoric acid and a salt (0.8-2 mole % W/V). Suitable preservatives include benzalkonium chloride (0.003-0.03 mole % W/V); chlorobutanol (0.3-0.9 mole % W/V); parabens (0.01-0.25 mole % W/V) and thimerosal (0.004-0.02 mole % W/V).

The present invention provides pharmaceutical compositions, for medical use, which comprise a polysaccharide preparation together with one or more therapeutic or prophylactic agents and, optionally, a pharmaceutically acceptable carruer and/or other therapeutic ingredients. The term "pharmaceutically-acceptable carruer" as used herein means one or more compatible solid or liquid filler, dilutants or encapsulating substances which are suitable for administration to a human or other animal. The components of the pharmaceutical compositions also are capable of being commingled with the formulations of the present invention, and with each other, in a manner such that there is no interaction which would substantially impair the desired pharmaceutical efficiency of the therapeutic or prophylactic agent in the formulation.

Controlled release of the active agent can also be achieved with appropriate excipient materials that are biocompatible and biodegradable. These polymeric materials which effect slow release of the active agent may be any suitable polymeric material for generating particles, including, but not limited to, nonbioerodable/non-biodegradable and bioerodable/biodegradable polymers. Such polymers have been described in great detail in the prior art. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, poly(methyl methacrylate), poly(ethylmethacrylate), poly(butylmethacrylate), poly(isobutylmethacrylate), poly (hexlmethacrylate), poly(isodecylmethacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene, polyvinylpryrrolidone, hyaluronic acid, and chondroitin sulfate.

Examples of preferred non-biodegradable polymers include ethylene vinyl acetate, poly(meth)acrylic acid, polyamides, copolymers and mixtures thereof.

Examples of preferred biodegradable polymers include synthetic polymers such as polymers of lactic acid and glycolic acid, polyanhydrides, poly(ortho)esters, polyurethanes, poly(butic acid), poly(valeric acid), poly(caprolactone), poly (hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. The most preferred polymers are polyesters, polyanhydrides, polystyrenes and blends thereof.

It has been found that the polysaccharide of the invention can deliver an effective amount of an active agent regardless of the size of the agent to be delivered. Thus, particles, e.g., particles which include a polysaccharide and an active agent, can be greater than 5, 10, 15, 20, 25, 30 microns and still be administered in vivo in therapeutically effective amounts by certain routes of administration, e.g., pulmonary delivery.

Pulmonary Administration

It was found that polysaccharides, e.g., based upon their chemical signature, can be modified to reduce one or more activity of the polysaccharide and used to generate enhanced formulations for delivering an active agent, e.g., a therapeutic or prophylactic agent, by a pulmonary route, e.g., by inhalation through the mouth or nasal passage. In addition, modification of the polysaccharide, e.g., by neutralizing or enhancing the net charge of a polysaccharide, such as an HLGAG, can enhance the ability of the active agent to permeate a lipid membrane, e.g., an alveolar membrane and/or epithelial barriers, of the lung. The term "pulmonary tissue" as used herein refers to any tissue of the respiratory tract and includes both the upper and lower respiratory tract, except where otherwise indicated.

Pulmonary delivery routes have several benefits including the ease of self-administration by a subject, e.g., the polysaccharide/active agent composition can be in a dosage unit form of the active agent. Dosage unit form as used herein refers to physically discrete units suited as unitary dosages for the subject to be treated; each unit containing a predetermined quantity of active agent calculated to produce the desired therapeutic effect. An example of a composition which can be used for self-administration include: metered amounts of a composition to be administered from an inhaler for pulmonary delivery. For example, metered amounts of a polysaccharide/insulin composition can provide therapeutically effective amounts of insulin to the subject having diabetes. In preferred embodiments, the polysaccharide is a heparin, e.g., a LMWH, e.g., ardeparin or enoxaparin, which has been modified to reduce anti-Xa and/or anti-IIa activity. The compositions can be included in a container, pack, or dispenser together with instructions for administration. These methods, as well as other methods used for pulmonary delivery, may also be used by health care professionals to administer the polysaccharide/active agent composition to a subject.

It is understood that the specific route of administration and dose level will depend upon a variety of factors including the activity of the specific agent employed, the age, body weight, general health, gender, and diet of the subject, the time of administration, the desired rate of absorption, bioavailability, the rate of excretion, any drug combination, and the location of desired therapeutic effect, e.g., local or systemic effect. A local therapeutic effect refers to a biologic effect that occurs at the tissue where the active agent is delivered. For instance, when the active agent is used for treating or preventing a localized reaction in the lung, it may be desirable to deliver the active agent to the lung to produce a local effect for the treatment of, e.g., a respiratory disease or a lung disease. A systemic effect refers to a biologic effect that occurs outside of the respiratory system where the active agent is delivered, e.g., the biological effect occurs after delivery to the blood.

For administration by inhalation, the polysaccharide/active agent composition can be delivered in the form of an aerosol spray from pressured container or dispenser which contains a suitable propellant or a nebulizer. The polysaccharide/active agent composition be in the form of a dry particle or as a liquid. Preferably, the polysaccharide/active agent composition is delivered to pulmonary tissue as a dry particle.

The polysaccharide/active agent composition may be conveniently delivered in the form of an aerosol spray presentation from pressurized packs or a nebulizer, with the use of a suitable propellant, e.g., dichlorodifluoromethane, trichlorofluoromethane, dielilorotetrafluoroctliane, carbon dioxide or other suitable gas. In the case of a pressurized aerosol, the dosage unit may be determined by providing a valve to deliver a metered amount of the active agent. Other devices can include those driven by patient aspiration. Capsules and cartridges for use in an inhaler or insufflator may be formulated containing a powder mix of the polysaccharide, the active agent and a suitable powder base such as lactose or starch, if the particle is a formulated particle. In addition, the polysaccharide/active agent compositions, can be administered with other materials such as 100% DPPC or other surfactants can be mixed with the polysaccharide/active agent composition to promote the delivery and dispersion of the active agent. Methods of preparing dry polysaccharide particles are described, for example, in PCT Publication WO 02/32406.

The polysaccharide/active agent composition when administered by pulmonary routes can result in the active agent being rapidly absorbed, thereby producing a rapid local or systemic therapeutic result. It has been discovered the polysaccharide can deliver an active agent such that the peak activity of the delivered active agent can be achieved within 3 to 4 hours, and preferably within two hours, after delivery. In some embodiments, the peak activity of the active agent can be achieved even more quickly, e.g., within one half hour or even within ten minutes. In some embodiments, the polysaccharide/active agent composition can be formulated for longer biological half-life of the active agent.

In one embodiment, the polysaccharide is delivered in an amount such that at least 5%, 10%, 15%, 20% or more of the polysaccharide/active agent composition is delivered to the upper lung. In other embodiments, at least 20%, 30%, 40%, 50%, 60%, 70%, or 80% of the polysaccharide/active agent composition is delivered to the upper lung. In one embodiment, the polysaccharide/active agent composition is provided in a metered dose using, e.g., an inhaler or nebulizer. Preferably, the active agent is delivered in a dosage unit form of at least about 0.5 mg of active agent/puff, 1 mg of active agent/puff, 2 mg of active agent/puff, 5 mg of active agent/puff, 10 mg of active agent/puff, 15 mg of active agent/puff, 20 mg of active agent/puff, 25 mg of active agent/puff, 30 mg of active agent/puff, 35 mg of active agent/puff, 40 mg of active agent/puff, 45 mg of active agent/puff, 50 mg of active agent/puff, 55 mg of active agent/puff, 60 mg of active agent/puff, 70 mg of active agent/puff, 80 mg of active agent/puff, 90 mg of active agent/puff, 100 mg of active agent/puff or more.

The percent bioavailability can be calculated as follows: the percent bioavailability=$(AUC_{non\text{-}invasive}/AUC_{i.v.\ or\ s.c.})\times(dose_{i.v.\ or\ s.c.}/dose_{non\text{-}invasive})\times 100$.

Although not necessary to achieve the desired levels of delivery, delivery enhancers such as surfactants can be used to enhance pulmonary delivery. A "surfactant" as used herein refers to a compound having a hydrophilic and lipophilic moiety, which promotes absorption of a drug by interacting with an interface between two immiscible phases. Surfactants are useful in the dry particles for several reasons, e.g., reduction of particle agglomeration, reduction of macrophage phagocytosis, etc. Surfactants are well known in the art and include but are not limited to phosphoglycerides, e.g., phosphatidylcholines, L-alpha-phosphatidylcholine dipalmitoyl (DPPC) and diphosphatidyl glycerol (DPPG); hexadecanol; fatty acids; polyethylene glycol (PEG); polyoxyethylene-9-; auryl ether; palmitic acid; oleic acid; sorbitan trioleate (Span 85); glycocholate; surfactin; poloxomer; sorbitan fatty acid ester; sorbitan trioleate; tyloxapol; phospholipids.

Methods for Monitoring Pulmonary Delivery

The amount of polysaccharide/active agent composition delivered can be determined using routine methods. For instance to determine delivery by inhalation, in a test system, lavage of animal lungs at indicated time intervals after inhalation can be used to determine the amount of polysaccharide/active agent delivered to the respiratory tract. These data can be correlated to that amount which would occur in humans or animals being treated. Alternatively, a label, such as a radioactive or fluorescent label can be attached to the polysaccharide (or active agent) and used to determine the distribution of the delivered polysaccharide/active agent composition. The amount of polysaccharide/active agent composition delivered to a desired tissue can also be determined as the amount of therapeutic effect resulting from the presence of the active agent in that tissue or in the region where the biological activity is occurring, e.g., the blood, or the blood plasma concentration of the active agent. The type of parameter used to assess the effectiveness of the delivery will vary depending on a variety of factors including the type of subject, the type of equipment available, and the disorder being treated or prevented. The peak plasma concentration of an active agent can be determined by measuring the level of active agent present in the blood over time and determining when the peak level of concentration is reached. The amount of a therapeutic effect or a peak plasma activity can be identified using routine assays. The type of these effects will depend on the therapeutic parameter being assessed. For instance, if a polysaccharide/insulin composition is administered in order to increase insulin levels, the amount of glucose and/or insulin in the blood can be assessed. Other assays are well known to those of ordinary skill in the art for various active agents.

Kits

Also within the scope of the invention are kits including a polysaccharide described herein along with instructions on how to use the polysaccharide. In some embodiments, the instructions include information on formulating a polysaccharide of the invention with an active agent. In other embodiments, the kit includes a formulation that includes a polysaccharide and an active agent (e.g., as described herein), and the instructions include information for using the formulation to treat, prevent or detect a disorder described herein. In some embodiments, the kit can include one or more other elements including: instructions for use; other reagents, e.g., a label, a therapeutic agent; devices or other materials for preparing the formulation for administration; pharmaceutically acceptable; devices or other materials for administration to a subject; and devices or other materials for monitoring the active agent. The instructions can include instructions for therapeutic application including suggested dosages and/or modes of administration, e.g., in a patient with a disorder described herein, e.g., diabetes, e.g., Type I or Type 2 diabetes. Other instructions can include instructions on coupling of the polysaccharide to an active agent. As discussed above, the kit can include an active agent, e.g., a therapeutic or prophylactic agent, e.g., any of the active agents described herein.

Therapeutic Uses

The compositions and formulations of the invention can be administered to a subject. As used herein, a subject is a vertebrate such as a human, non-human primate, cow, horse, pig, sheep, goat, dog, cat, rabbit, or rodent. The subject can be, e.g., an experimental animal, a veterinary animal, or a human subject.

The pharmaceutical compositions of the invention may include a "therapeutically effective amount" or a "prophylactically effective amount" of an active agent. A "therapeutically effective amount" refers to an amount effective, at dosages and for periods of time necessary, to achieve the desired therapeutic result. A therapeutically effective amount of the active agent may vary according to factors such as the disease state, age, sex, and weight of the individual, and the ability of the active agent to elicit a desired response in the individual. A therapeutically effective amount is also one in which any toxic or detrimental effects of the active agent are outweighed by the therapeutically beneficial effects. A "therapeutically effective dosage" preferably inhibits a measurable parameter, relative to untreated subjects. The ability of a compound to inhibit a measurable parameter can be evaluated in an animal model system predictive of efficacy in human. Alternatively, this property of a composition can be evaluated by examining the ability of the active agent to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The polysaccharide/active agent includes an active agent other than polysaccharides having at least one reduced activity. These include, for instance, but are not limited to, active agents such as proteins, nucleic acids, small organic or inorganic molecules, that do not have slow release properties, preservatives, etc. Examples of small molecules include, but are not limited to, peptides, peptidomimetics (e.g., peptoids), amino acids, amino acid analogs, polynucleotides, polynucleotide analogs, nucleotides, nucleotide analogs, organic and inorganic compounds (including heterorganic and organomettallic compounds) having a molecular weight less than about 5,000 grams per mole, organic or inorganic compounds having a molecular weight less than about 2,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Thus, the methods relate to pulmonary administration of active agents. An active agent as used herein is any compound which has a diagnostic, prophylactic, or therapeutic effect in a biological organism. The active agents may optionally be proteins, peptides, antibodies, polysaccharides, nucleic acids (e.g., RNA, DNA, PNA, multiplexes of them (e.g.: triplex)), saccharides, glycoproteins, amino acids, viruses, heterogeneous mixtures of macromolecules (e.g., a natural product extract) and hybrid macromolecules (e.g., protein/nucleic acid hybrids, albumin conjugated proteins, drugs with linker inorganic molecules, organic molecules, lipids, glycolipids, or combinations thereof.

A bioactive agent is any compound which has a prophylactic or therapeutic effect in a biological organism. In some embodiments the bioactive agent is any of the drugs described above or one or more of the following agents: adrenergic agent; adrenocortical steroid; adrenocortical suppressant; agents for treating cognition, antiplatelets, aldosterone antagonist; amino acid; anabolic; analeptic; analgesic; anesthetic; anorectic; anti-acne agent; anti-adrenergic; anti-allergic; anti-Alzheimer's, anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; anxiolytics, appetite suppressant; blood glucose regulator; bone resorption inhibitor; bronchodilator; cardiovascular agent; cholinergic; COX1 inhibitors, COX2 inhibitors, direct thrombin inhibitors, depressant; diagnostic aid; diuretic; dopaminergic agent; estrogen receptor agonist; fibrinolytic; fluorescent agent; free oxygen radical scavenger; gastrointestinal motility effector; glucocorticoid; GPIIbIIIa antagonists, hair growth stimulant; hemostatic; histamine H2 receptor antagonists; hormone; human growth hormone, hypocholesterolemic; hypoglycemic; hypolipidemic; hypnotics, hypotensive; imaging agent; immunological agents such as immunizing agents, immunomodulators, immunoregulators, immunostimulants, and immunosuppressants; cytokines, e.g., interferons; insulin; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; proton pump inhibitors, psychotropic; radioactive agent; scabicide; sclerosing agent; sedative; sedative-hypnotic; selective adenosine A1 antagonist; serotonin antagonist; serotonin inhibitor; serotonin receptor antagonist; statins, steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor. In preferred embodiments, the active agent is a polypeptide having a moleular weigh of about 5 to 10 kD, 20 to 40 kD, 60 to 80 kD, 100 to 150 kD or more.

In some embodiments, at least a portion of the therapeutic or prophylactic agent is delivered to the upper lung, e.g., at least 5%, 10%, 20%, 30%, 40%, 50%, 60%, 70%, 80%, 90% or more of the therapeutic or prophylactic agent is delivered to the upper lung. In some embodiments, the bioavailability of the therapeutic or prophylactic agent is at least 5%, 10%, 20%, 30%, 40%, 50%, 60%, 70%, 80%, 90% greater than the bioavailability of the therapeutic or prophylactic agent in the absence of the polysaccharide.

The formulations and compositions can further include interferon as the active agent. The indications for interferon treatment can include the relapsing forms of multiple sclerosis. Other indications include: a cancer (e.g., cancer of the kidney, melanoma, multiple myeloma, carcinoid tumors, lymphoma and leukemia), or hepatitis (e.g., hepatitis B and hepatitis C).

In some embodiments, the active agent is insulin and the disorder being treated is diabetes. The term "diabetes" or "diabetes mellitus" is intended to have its medical meaning, namely, a metabolic disorder of multiple etiology characterized by chronic hyperglycemia with disturbances of carbohydrate, fat and protein metabolism resulting from defects in insulin secretion, insulin action, or both. Symptoms of Type 1 diabetes include polyuria, polydipsia, blurring of vision and unexplained weight loss. Symptoms of Type 2 diabetes include hyperglycemia, hyperinsulinemia and obesity. A diagnosis of diabetes is often made when any three of these tests is positive, followed by a second positive test on a different day:

Fasting plasma glucose of greater than or equal to 126 mg/dl with symptoms of diabetes.

Casual plasma glucose (taken at any time of the day) of greater than or equal to 200 mg/dl with the symptoms of diabetes.

Oral glucose tolerance test (OGTT) value of greater than or equal to 200 mg/dl measured at a two-hour interval. The OGTT is given over a three-hour time span.

The effects of diabetes mellitus include long-term damage, dysfunction and failure of various organs. In its most severe forms, ketoacidosis or a non-ketotic hyperosmolar state may develop and lead to stupor, coma and, in absence of effective treatment, death. Often symptoms are not severe, or may be absent, and consequently hyperglycemia sufficient to cause pathological and functional changes may be present for a long time before the diagnosis is made. The long-term effects of diabetes mellitus include progressive development of the specific complications of retinopathy with potential blindness, nephropathy that may lead to renal failure, and/or neuropathy with risk of foot ulcers, amputation, Charcot joints, and features of autonomic dysfunction, including sexual dysfunction. People with diabetes are at increased risk of cardiovascular, peripheral vascular and cerebrovascular disease.

Several pathogenetic processes are involved in the development of diabetes. The abnormalities of carbohydrate, fat and protein metabolism are due to deficient action of insulin on target tissues resulting from insensitivity or lack of insulin. Pathological indications of Type I diabetes include a reduction in number and/or size of pancreatic islet β-cells and high presence of lymphatic infiltrates in an around the islets. These lead to consequent insulin deficiency and glucose intolerance. The pathology of Type 2 diabetes includes fibrotic and/or amylin deposits in the islets of the pancreas, and/or a reduction in the size or number of pancreatic islet β-cells.

The methods of the invention include administering by pulmonary delivery a formulation that includes a heparin and insulin to a subject having diabetes such that the bioavailability of the insulin is at least about 10 to 100,000 μIU/ml over a period of about 5 minutes to 5 hours, preferably in a period of less than 1 to 2 hours after delivery. Such methods can include, e.g., delivering a metered dose of the formulation such that each dose includes 0.5 IU/kg insulin, 1 IU/kg insulin, 5 IU/kg insulin, 10 IU/kg insulin, 20 IU/kg insulin, 30 IU/kg insulin, 50 IU/kg insulin, 75 IU/kg insulin, 100 IU/kg insulin, 150 IU/kg insulin, 200 IU/kg insulin, 250 IU/kg insulin, 300 IU/kg insulin, and integers in between.

In some embodiments, the active agent is human growth hormone (i.e., Somatotropin). There are several indications for growth hormone treatment, including GHD, cardiovascular risk associated with GHD, pediatric growth failure and Turner's syndrome, and adult HGH deficiency due to pituitary disease, hypothalamic disease, surgery, trauma, radiation therapy, chronic renal insufficiency, Prader-Willi syndrome or growth retardation in children with GHD. In other embodiments, patients include adults who had inadequate growth hormone as children and subsequently identified as growth hormone deficient. In other embodiments, patients include those suffering from AIDS wasting and/or chemotherapy. Other disorders that can be treated or prevented with a polysaccharide/human growth hormone formulation include: pituitary disease (e.g., pituitary tumor, pituitary surgical damage, hypothalmic disease, irradiation or trauma to the pituitary); fatigue syndromes; fibromyalgia; and obesity. Pituitary hypothalmic diseases include subjects with Sheehan's syndrome, autoimmune hypophysitis, or hypophysitis associated with inflammatory conditions such as sarcoidosis.

Patients having GHD have reduced or absent levels of human growth hormone and IGF-I. In growth hormone deficient adults, the effect of the fatty tissue in the absence of growth hormone is increased body fat. The increase in body fat and the absence of IGF-I can produce insulin resistance. The lack of growth hormone and IGF-I in muscle and bone can also result in decreased muscle mass and bone density. The absence of growth hormone and IGF-I can also lead to increased risk of cardiovascular disorders, sometime resulting in death. Various test are available for diagnosing GHD including insulin tolerance tests, and tests utilizing arginine and the hypothalamic releasing hormone for growth hormone, namely GHRH. Such tests are described in the "American Association of Clinical Endocrinologists Medical Guidelines fro Clinical Practice for Growth Hormone Use in Adults and Children-2003 Update", *Endocrinology Practice* 9(1): 64-76. GHD treatment can be monitored by one or more of the following: increased human growth hormone levels; increased IGF-I levels; increased bone density; increased lean tissue; decreasing adipose tissue; increased cardiac contractility; and enhanced exercise capability.

The polysaccharide/human growth hormone formulations described herein can also be used to treat Turner's syndrome. Turner's syndrome is a disorder affecting girls that is caused by abnormalities of or the absence of an X chromosome. It is frequently associated with short stature. Other symptoms include: shortness of the neck, webbing of the neck, cubitus valgus, shortness of the fourth or fifth metacarpels and metatarsals, a shield shaped chest, and primary hypogonadism.

In some embodiments, the active agent is EPO. Indications for EPO include, for example, anaemia, which can be a disease in its own right or a symptom of another disease.

In other embodiments, a polysaccharide can be chosen for pulmonary delivery that decreases systemic delivery of the agent as compared to pulmonary delivery of the agent in the absence of the polysaccharide. Such formulations can be used, e.g., for local delivery of an active agent, e.g., a therapeutic or prophylactic agent to the pulmonary tissue. These formulations can be valuable, e.g., in treatment of respiratory diseases such as cystic fibrosis, asthma, allergy, emphysema, adult respiratory distress syndrome (ARDS), lung reperfusion injury, idiopathic pulmonary fibrosis, and asbestos-related fibrosis (e.g., black or brown lung).

Cystic fibrosis is a chronic progressive disease affecting the respiratory system. One serious consequence of cystic fibrosis is *Pseudomonas aeruginosa* lung infection, which by itself accounts for almost 90% of the morbidity and mortality in cystic fibrosis. Therapeutics for treating cystic fibrosis include antimicrobials for treating the pathogenic infection. The formulations described herein can be used to deliver such antimicrobials or other agents useful for treating cystic fibrosis to the lung of a subject having cystic fibrosis.

Asthma is a chronic lung condition characterized by difficulty in breathing. In general, subjects with asthma have extra sensitive or hyperresponsive airways. The airways react by narrowing or obstructing when they become irritated, which creates difficulty for movement of the air in and out of the lungs. This narrowing or obstruction is caused by one or more of airway inflammation (meaning that the airways in the lungs become red, swollen and narrow), and bronchoconstriction (meaning that the muscles that encircle the airways tighten or go into spasm). The following symptoms are associated with asthma: wheezing, coughing, shortness of breath, and chest tightness. The formulations described herein can be used to deliver such therapeutic agents useful for treating asthma to the lung of a subject having asthma.

Pulmonary cancers are broadly classified into small cell or non-small cell. Non-small cell cancers are further divided into adenocarcinomas, bronchoalveolar-alveolar, squamous cell and large cell carcinomas. Approximately, 75-85 percent of lung cancers are non-small cell cancers and 15-25 percent are small cell cancers of the lung. About eighty percent of pulmonary cancers are due to tobacco smoke. Symptoms that may indicate the pulmonary cancer has spread include hoarseness of the voice (due to spread of the cancer to nerves which control the vocal cords), difficulty in swallowing, and swelling of the face, arms and neck. Metastatic spread of the cancer outside the lung and chest can occur with any of the lung cancer types, but most commonly with small cell cancers and adenocarcinomas. Headaches, weakness, numbness or paralysis may indicate spread of the cancer to the brain or spinal cord. Bone pain or pain in the abdomen can be symptoms of cancer spread to these areas. The formulations described herein can be used to deliver such therapeutic agents useful for pulmonary cancer to the lung of a subject having pulmonary cancer.

Pulmonary infections include a variety of disorders including tuberculosis, pneumonia, bronchitis, anthrax infection, *Pseudomonas aerginosa*, etc. The formulations described herein can be used to deliver such therapeutic agents useful for pulmonary infection, for example one or more antibiotics, to the lung of a subject suffering from pulmonary infection.

A number of embodiments of the invention have been described. Nevertheless, it will be understood that various modifications may be made without departing from the spirit and scope of the invention. Accordingly, other embodiments are within the scope of the following claims.

What is claimed:

1. A formulation for pulmonary delivery of a therapeutic or diagnostic polypeptide comprising a therapeutic or diagnostic polypeptide and a LMWH produced by a method that includes depolymerization and having an average molecular weight of less than 8000 Da, wherein the LMWH is linked to the polypeptide and the formulation is provided in a device for pulmonary delivery.

2. The formulation of claim 1, wherein the LMWH is chosen from the group of: enoxaparin, dalteparin, reviparin, tinzaparin, nadroparin, certoparin, ardeparin, and parnaparin.

3. The formulation of claim 1, wherein the LMWH comprises a hexasaccharide or larger polysaccharide.

4. The formulation of claim 1, wherein the LMWH comprises an octasaccharide or larger polysaccharide.

5. The formulation of claim 1, wherein the polypeptide is selected from the group consisting of: insulin, proinsulin, human growth hormone, interferon, α-1 proteinase inhibitor, alkaline phosphotase, angiogenin, cystic fibrosis transmembrane conductance regulator, extracellular superoxide dismutase, fibrogen, glucocerebrosidase, glutamate decarboxylase, human serum albumin, myelin basic protein, soluble CD4, lactoferrin, lactoglobulin, lysozyme, lactoalbumin, erythropoietin, tissue plasminogen activator, antithrombin III, prolactin, and α1-antitrypsin.

6. The formulation of claim 1, wherein polypeptide is selected from the group consisting of: parathyroid hormone and derivatives and fragments thereof, erythropoietin, epoetin beta, gene activated erythropoietin, epoetin beta, second generation EPO, epoetin beta, novel erythropoiesis stimulating protein, insulin lispro, insulin (bovine), insulin, insulin aspart, insulin analogue, Calcitonin, Theraccine, becaplermin (recombinant human platelet derived growth factor-BB), trafermin, human growth hormone-releasing factor, BMP-7, PEG aspariginase, dornase alpha, alglucerase, agalsidase-beta, dornase alpha, agalsidase-alfa, streptokinase, teneteplase, reteplase, alteplase, pamiteplase, Rh factor VIII, Rh FVIIa, Factor TX (Human), Factor IX (complex), HGH, Somatrem/somatropin, Anti-CD33- calicheamicin conjugate, Edrecolomab, rituxumab, daclizumab, trastuzumab, sulesomab, abciximab, infliximab, muromonab-CD3, palivizumab, alemtuzumab, basiliximab, oprelvekin, gemtuzumab ozogamicin, ibritumomab tiuxetan, sulesomab, palivizumab, interleukin-2, celmoleukin (rIL-2), interferon alfacon-1, interferon alpha, interferon alpha+ribavirin, peg interferon alpha-2a, interferon alpha-2b, interferon alpha 3n, interferon beta-1a, interferon beta, interferon beta 1b, interferon gamma, interferon gamma-1b, filgrastim, lenograstim, sargramostim, molgramostim, mirimostim, sargramostim, nartograstim, oprelvekin, peptide tyrosin-tyrosin (PYY), apolipoprotein A-IV, leptin, melanocortin, amylin, orexin, adiponectin, and ghrelin.

7. The formulation of claim 1, wherein the therapeutic polypeptide has a molecular weight of about 500 Da to 5 kDa, 5 to 10 kDa, 10 to 20 kDa, 20 to 40 kDa, 50 to 100 kDa, or 100 to 150 kDa.

8. The formulation of claim 7, wherein the polypeptide has a molecular weight of less than 150 kD.

9. The formulation of claim 7, wherein the polypeptide has a molecular weight of 0.5-35 kDa.

10. The formulation of claim 1, further comprising a delivery enhancer.

11. The formulation of claim 1, wherein the formulation is provided in a pressurized container or dispenser.

12. The formulation of claim 1, wherein the LMWH has been modified to alter one or more of its charge, size or therapeutic activity.

13. The formulation of claim 1, wherein all or a portion of the polysaccharides in the LMWH consists of about two to twenty disaccharides.

14. The formulation of claim 1, wherein a chemical signature of one or more of the polysaccharides in the LMWH has been determined and one or more polysaccharide is modified based upon its chemical signature.

15. The formulation of claim 1, wherein a chemical signature of one or more of the polysaccharide in the LMWH has been determined.

16. The formulation of claim 1, wherein the LMWH comprises one or more chemical signatures of a oligosaccharide having a structure selected from the group consisting of $\Delta UH_{NAC,6S}GH_{NS,3S,6S}$, $\Delta UH_{NS,6S}GH_{NS,3S,6S}$, $\Delta UH_{NAc,6S}GH_{NS,3S}$, and $\Delta UH_{NS,6S}GH_{NS,3S}$.

17. The formulation of claim 1, wherein the therapeutic polypeptide is linked to polysaccharide by one or more of EDC or CNBH4/DMSO/Acetic Acid.

18. The formulation of claim 1, wherein the formulation is a dry formulation.

19. The formulation of claim 18, wherein the dry formulation comprises LMWH particles having a mean geometric diameter of 1 to 500 microns.

20. The formulation of claim 19, wherein the LMWH particles have a mean geometric diameter of at least 2 to 100 microns.

21. The formulation of claim 1, wherein the formulation is a liquid formulation, an aerosol, a mist, or a suspension.

22. A method of preparing a formulation for pulmonary delivery of a therapeutic or diagnostic polypeptide, the method comprising:

combining a therapeutic or diagnostic polypeptide, and a LMWH produced by a method that includes depolymerization and having an average molecular weight of less than 8000 Da, wherein the polypeptide and the LMWH are present in amounts sufficient for pulmonary delivery of the polypeptide, and wherein the LMWH is combined with the therapeutic polypeptide by linking the LMWH and the therapeutic polypeptide, to thereby prepare a formulation for pulmonary delivery of the polypeptide.

23. The method of claim 22, wherein the LMWH has anti-Xa activity and/or anti-IIa activity that is reduced by at least 50%, or more as compared to a reference standard and the reference standard is the level of anti-Xa activity and/or anti-IIa activity of a commercially available version of the heparin selected from the group consisting of unfractionated heparin, enoxaparin, dalteparin, reviparin, tinzaparin, nadroparin, certoparin, ardeparin, and parnaparin.

24. The method of claim 22, wherein the LMWH consists of about two to twenty disaccharides.

25. The method of claim 23, wherein the LMWH further comprises a size that is reduced as compared to the reference standard.

26. The method of claim 23, wherein the LMWH further comprises a charge that has been modified as compared to the reference standard.

27. The method of claim 22, wherein the LMWH is combined with a therapeutic polypeptide selected from the group consisting of: insulin, proinsulin, human growth hormone, interferon, α-1 proteinase inhibitor, alkaline phosphotase, angiogenin, cystic fibrosis transmembrane conductance regulator, extracellular superoxide dismutase, fibrogen, glucocerebrosidase, glutamate decarboxylase, human serum albumin, myelin basic protein, soluble CD4, lactofeffin, lactoglobulin, lysozyme, lactoalbumin, erythropoietin, tissue plasminogen activator, antithrombin III, prolactin, and α1-antitrypsin.

28. The method of claim 22, wherein the LMWH is combined with the therapeutic polypeptide selected from the group consisting of: parathyroid hormone and derivatives and fragments thereof, erythropoietin, epoetin beta, gene activated erythropoietin, epoetin beta, second generation EPO, epoetin beta, novel erythropoiesis stimulating protein, insulin lispro, insulin (bovine), insulin, insulin aspart, insulin analogue, Calcitonin, Theraccine, becaplermin (recombinant human platelet derived growth factor-BB), trafermin, human growth hormone-releasing factor, BMP-7, PEG aspariginase, dornase alpha, alglucerase, agalsidase-beta, dornase alpha, agalsidase-alfa, streptokinase, teneteplase, reteplase, alteplase, pamiteplase, Rh factor VIII, Rh FVIIa, Factor TX (Human), Factor IX (complex), HGH, Somatrem/somatropin, Anti-CD33-calicheamicin conjugate, Edrecolomab, rituxumab, daclizumab, trastuzumab, sulesomab, abciximab, infliximab, muromonab-CD3, palivizumab, alemtuzumab, basiliximab, oprelvekin, gemtuzumab ozogamicin, ibritumomab tiuxetan, sulesomab, palivizumab, interleukin-2, celmoleukin (rIL-2), interferon alfacon-1, interferon alpha, interferon alpha+ribavirin, peg interferon alpha-2a, interferon alpha-2b, interferon alpha 3n, interferon beta-1a, interferon beta, interferon beta 1b, interferon gamma, interferon gamma-1b, filgrastim, lenograstim, sargramostim, molgramostim, mirimostim, sargramostim, nartograstim, oprelvekin, peptide tyrosin-tyrosin (PYY), apolipoprotein A-IV, leptin, melanocortin, amylin, orexin, adiponectin, and ghrelin.

29. The method of claim 22, wherein the polypeptide has a molecular weight of about 500 Da to 5 kDa, 5 to 10 kDa, 10 to 20 kDa, 20 to 40 kDa, 50 to 100 kDa, or 100 to 150 kDa.

30. The method of claim 29, wherein the polypeptide has a molecular weight of less than 150 kD.

31. The method of claim 29, wherein the polypeptide has a molecular weight of 0.5-35 kDa.

32. The method of claim 22, further comprising combining the formulation with one or more delivery enhancers.

33. The method of claim 22, further comprising providing formulation in a device for pulmonary delivery.

34. The method of claim 33, wherein the device for pulmonary delivery is a pressurized container or dispenser.

35. The method of claim 22, wherein the LMWH is modified at one or more chemical signature of a oligosaccharide of the heparin which comprises the structure: $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$, to reduce the anti-Xa activity of the heparin.

36. The method of claim 22, wherein the LMWH is modified at one or more chemical signature of a oligosaccharide of the heparin which comprises the structure: $\Delta UH_{NAc,6S}GH_{NS,3S,6S}$ and $\Delta UH_{NAc,6S}GH_{NS,3S}$ to reduce the anti-Xa activity of the heparin.

37. The method of claim 35, wherein the LMWH comprises one or more monosaccharide or disaccharide which have been added or removed from the structure, or one or more acetyl group and/or sulfo group has been substituted, added or removed from the structure.

38. The method of claim 22, wherein the therapeutic polypeptide is linked to the LMWH by one or more of EDC or CNBH4/DMSO/Acetic Acid.

39. The method of claim 22, wherein the LMWH comprises a hexasaccharide or larger polysaccharide.

40. The method of claim 22, wherein the LMWH comprises an octasaccharide or larger polysaccharide.

41. A formulation for pulmonary delivery of human growth hormone comprising human growth hormone and a LMWH produced by a method that includes depolymerization and having an average molecular weight of less than 8000 Da, wherein the formulation is provided in a device for pulmonary delivery.

42. A method of preparing a formulation for pulmonary delivery of human growth factor, the method comprising:

combining human growth factor, and a LMWH produced by a method that includes depolymerization and having an average molecular weight of less than 8000 Da, wherein the polypeptide and the LMWH are present in amounts sufficient for pulmonary delivery of human growth factor, to thereby prepare a formulation for pulmonary delivery of human growth factor.

43. A formulation for pulmonary delivery of human growth factor comprising human growth factor and a LMWH wherein the LMWH is produced by a method that includes depolymerization, the LMWH has an average molecular weight of less than 8000 Da, and the LMWH has anti-Xa activity and/or anti-IIa activity that is reduced by at least 50%, or more as compared to the level of anti-Xa activity and/or anti-IIa activity of a commercially available version of a heparin selected from the group consisting of unfractionated heparin, enoxaparin, dalteparin, reviparin, tinzaparin, nadroparin, certoparin, ardeparin, and parnaparin, wherein the anti-Xa activity and/or anti-ha activity is reduced by modification of at one or more chemical signature that comprises the structure: $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$, and wherein the formulation is provided in a device for pulmonary delivery.

* * * * *